US010653458B2

(12) United States Patent
Tanaka et al.

(10) Patent No.: US 10,653,458 B2
(45) Date of Patent: May 19, 2020

(54) METHODS FOR IMPLANTING A BONE SCREW

(71) Applicant: Providence Medical Technology, Inc., Pleasanton, CA (US)

(72) Inventors: Shigeru Tanaka, Half Moon Bay, CA (US); Jeffrey D. Smith, Clayton, CA (US); Christopher U. Phan, Dublin, CA (US); Edward Liou, Pleasanton, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 225 days.

(21) Appl. No.: 15/954,211

(22) Filed: Apr. 16, 2018

(65) Prior Publication Data

US 2018/0360518 A1   Dec. 20, 2018

Related U.S. Application Data

(63) Continuation of application No. 14/709,425, filed on May 11, 2015, now Pat. No. 9,943,342.

(51) Int. Cl.
*A61B 17/88* (2006.01)
*A61B 17/70* (2006.01)
(Continued)

(52) U.S. Cl.
CPC ...... *A61B 17/7082* (2013.01); *A61B 17/8605* (2013.01); *A61B 17/8875* (2013.01);
(Continued)

(58) Field of Classification Search
CPC combination set(s) only.
See application file for complete search history.

(56) References Cited

U.S. PATENT DOCUMENTS 4,604,995 A   8/1986 Stephens et al.
5,584,832 A   12/1996 Schlapfer et al.
(Continued)

FOREIGN PATENT DOCUMENTS

FR   2941365 A1   7/2010
WO   9641582 A1   12/1996
(Continued)

OTHER PUBLICATIONS

International Search Report and Written Opinion dated Aug. 16, 2016 in connection with International Patent Application No. PCT/US2016/031821, 14 pages.
(Continued)

*Primary Examiner* — Christian A Sevilla
(74) *Attorney, Agent, or Firm* — Dorsey & Whitney LLP

(57) ABSTRACT

A method for implanting a bone screw in a vertebra may first involve inserting the bone screw and a bone screw delivery mechanism through a proximal end of a guide tube along a first trajectory. A proximal end of the bone screw is attached to a distal end of the bone screw delivery mechanism, and a distal end of the guide tube is positioned adjacent the vertebra. The method may next involve advancing the bone screw and the bone screw delivery mechanism through a bend in the guide tube to cause the bone screw to exit the distal end of the guide tube along a second trajectory and contact the vertebra. The method may further involve rotating the delivery mechanism to cause the bone screw to screw into the vertebra and detaching the bone screw delivery mechanism from the bone screw.

14 Claims, 20 Drawing Sheets

(51) Int. Cl.
*A61B 17/86* (2006.01)
*A61F 2/46* (2006.01)
*A61B 17/17* (2006.01)
*A61B 90/00* (2016.01)
*A61F 2/30* (2006.01)

(52) U.S. Cl.
CPC ......... *A61F 2/4611* (2013.01); *A61B 17/1728* (2013.01); *A61B 17/1757* (2013.01); *A61B 17/7064* (2013.01); *A61B 17/864* (2013.01); *A61B 17/8685* (2013.01); *A61B 17/8886* (2013.01); *A61B 17/8888* (2013.01); *A61B 2090/037* (2016.02); *A61F 2/4603* (2013.01); *A61F 2002/30558* (2013.01); *A61F 2002/30593* (2013.01); *A61F 2002/30782* (2013.01); *A61F 2002/30784* (2013.01); *A61F 2002/30904* (2013.01); *A61F 2002/4625* (2013.01); *A61F 2002/4627* (2013.01); *A61F 2002/4638* (2013.01)

(56) References Cited

U.S. PATENT DOCUMENTS

| | | | |
|---|---|---|---|
| 5,941,885 A | 8/1999 | Jackson | |
| 5,971,987 A * | 10/1999 | Huxel | A61B 17/8605 411/2 |
| 6,068,642 A * | 5/2000 | Johnson | A61B 17/1615 606/180 |
| 6,179,841 B1 | 1/2001 | Jackson | |
| 6,419,678 B1 | 7/2002 | Asfora | |
| 6,565,605 B2 | 5/2003 | Fallin et al. | |
| 6,726,687 B2 | 4/2004 | Jackson | |
| 6,783,004 B1 * | 8/2004 | Rinner | A61B 17/8875 206/368 |
| 6,974,478 B2 | 12/2005 | Reiley et al. | |
| 7,090,698 B2 | 8/2006 | Fallin et al. | |
| 7,527,638 B2 | 5/2009 | Anderson et al. | |
| 7,682,393 B2 * | 3/2010 | Trieu | A61B 17/1631 623/17.11 |
| 7,947,045 B2 | 5/2011 | Hestad et al. | |
| 8,123,751 B2 | 2/2012 | Shluzas | |
| 8,152,714 B2 | 4/2012 | Garcia-Bengochea et al. | |
| 8,313,528 B1 | 11/2012 | Wensel | |
| 8,328,815 B2 | 12/2012 | Farr et al. | |
| 8,333,770 B2 | 12/2012 | Hua | |
| 8,382,839 B1 | 2/2013 | Wensel | |
| 8,388,659 B1 | 3/2013 | Lab et al. | |
| 8,523,945 B1 | 9/2013 | Wensel | |
| 8,551,175 B1 | 10/2013 | Wensel | |
| 8,556,940 B2 | 10/2013 | Hua | |
| 8,597,299 B2 | 12/2013 | Farr et al. | |
| 8,721,691 B2 | 5/2014 | Hua | |
| 8,747,412 B2 | 6/2014 | Bae et al. | |
| 8,753,377 B2 | 6/2014 | Liou et al. | |
| 8,814,913 B2 | 8/2014 | Jackson | |
| 8,834,472 B2 | 9/2014 | Liou et al. | |
| 8,870,879 B2 | 10/2014 | Han et al. | |
| 8,870,882 B2 | 10/2014 | Kleiner | |
| 9,072,563 B2 | 7/2015 | Luby et al. | |
| 9,186,193 B2 | 11/2015 | Kleiner et al. | |
| 9,314,283 B2 | 4/2016 | Overes et al. | |
| 9,358,127 B2 | 6/2016 | Duffield et al. | |
| 9,730,805 B1 | 8/2017 | Wensel et al. | |
| 9,943,342 B2 | 4/2018 | Tanaka et al. | |
| 10,149,710 B2 | 12/2018 | Tanaka et al. | |
| 2005/0149192 A1 | 7/2005 | Zucherman et al. | |
| 2006/0036259 A1 * | 2/2006 | Carl | A61B 17/70 606/90 |
| 2006/0039772 A1 | 2/2006 | Matthys-mark | |
| 2006/0083603 A1 | 4/2006 | Jackson | |
| 2006/0085002 A1 * | 4/2006 | Trieu | A61B 17/1631 623/17.11 |
| 2006/0241602 A1 | 10/2006 | Jackson | |
| 2007/0050031 A1 | 3/2007 | Khosrowshahi | |
| 2007/0250167 A1 | 10/2007 | Bray et al. | |
| 2008/0033440 A1 * | 2/2008 | Moskowitz | A61B 17/8875 606/251 |
| 2008/0154377 A1 | 6/2008 | Voellmicke | |
| 2009/0222092 A1 | 9/2009 | Davis et al. | |
| 2010/0076500 A1 | 3/2010 | Bray et al. | |
| 2010/0114105 A1 | 5/2010 | Butters et al. | |
| 2010/0191241 A1 * | 7/2010 | McCormack | A61F 2/4405 606/83 |
| 2011/0230971 A1 | 9/2011 | Donner et al. | |
| 2011/0282390 A1 | 11/2011 | Hua et al. | |
| 2012/0078373 A1 | 3/2012 | Gamache et al. | |
| 2012/0116466 A1 | 5/2012 | Dinville et al. | |
| 2012/0150301 A1 | 6/2012 | Gamache et al. | |
| 2012/0203290 A1 | 8/2012 | Warren et al. | |
| 2012/0265259 A1 | 10/2012 | LaPosta et al. | |
| 2013/0103095 A1 * | 4/2013 | Brumfield | A61B 17/7064 606/279 |
| 2013/0144347 A1 | 6/2013 | Jackson | |
| 2013/0226300 A1 | 8/2013 | Chataigner et al. | |
| 2014/0012380 A1 | 1/2014 | Laurence et al. | |
| 2014/0031872 A1 | 1/2014 | Jackson | |
| 2014/0074241 A1 | 3/2014 | McConnell et al. | |
| 2014/0081335 A1 | 3/2014 | Jackson et al. | |
| 2014/0214097 A1 | 7/2014 | Jackson et al. | |
| 2014/0236237 A1 | 8/2014 | Mahajan et al. | |
| 2014/0276891 A1 | 9/2014 | DeFalco et al. | |
| 2014/0277196 A1 | 9/2014 | Foley et al. | |
| 2014/0277472 A1 | 9/2014 | Gray et al. | |
| 2014/0330314 A1 | 11/2014 | Tsuang et al. | |
| 2015/0094770 A1 | 4/2015 | Jackson et al. | |
| 2015/0209089 A1 | 7/2015 | Bernard et al. | |
| 2015/0297357 A1 | 10/2015 | McCormack et al. | |
| 2015/0305781 A1 | 10/2015 | Landry et al. | |
| 2015/0305887 A1 | 10/2015 | Hickey et al. | |
| 2016/0100951 A1 | 4/2016 | Suddaby et al. | |
| 2016/0331418 A1 * | 11/2016 | Tanaka | A61B 17/8875 |
| 2016/0331553 A1 * | 11/2016 | Tanaka | A61B 17/8605 |
| 2017/0027713 A1 | 2/2017 | Kleiner | |
| 2017/0172639 A1 | 6/2017 | DeFalco et al. | |
| 2018/0360518 A1 | 12/2018 | Tanaka et al. | |
| 2019/0209227 A1 | 7/2019 | Tanaka et al. | |

FOREIGN PATENT DOCUMENTS

| | | |
|---|---|---|
| WO | 0053126 A1 | 9/2000 |
| WO | 0234120 A2 | 5/2002 |
| WO | 2009033100 A1 | 3/2009 |
| WO | 2014089535 A1 | 6/2014 |
| WO | 2016007412 A1 | 1/2016 |

OTHER PUBLICATIONS

Stein, et al., "Percutaneous Facet Joint Fusion: Preliminary Experience," Journal of Vascular and Interventional Radiology, Jan.-Feb. 1993, pp. 69-74, vol. 4, No. 1.

* cited by examiner

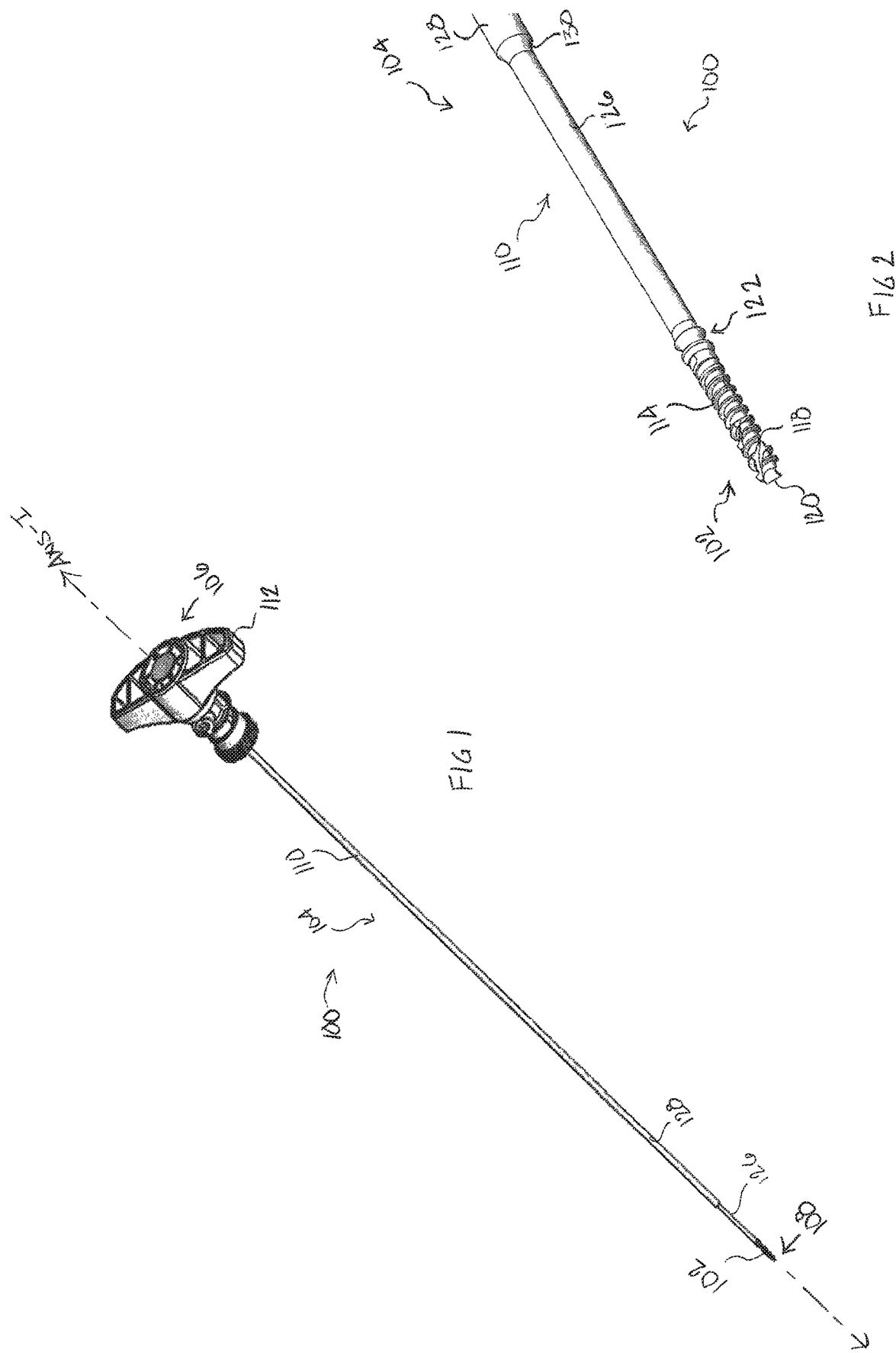

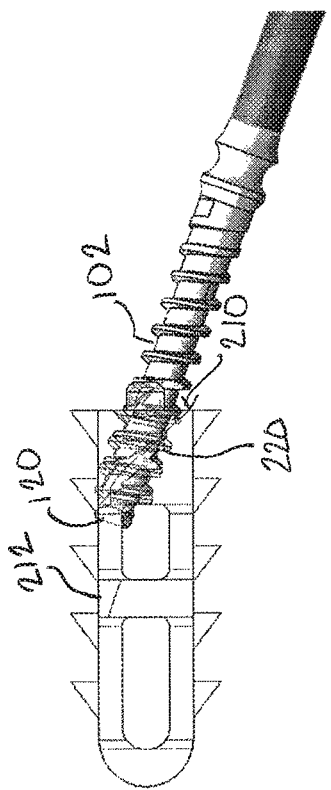
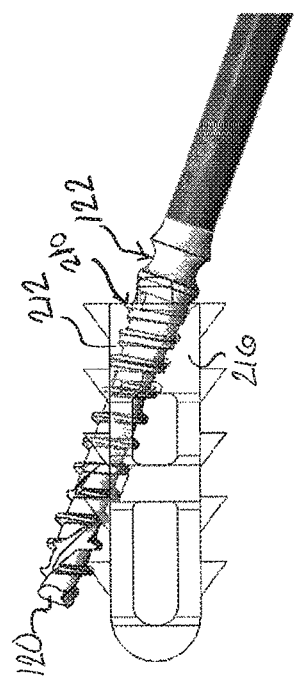
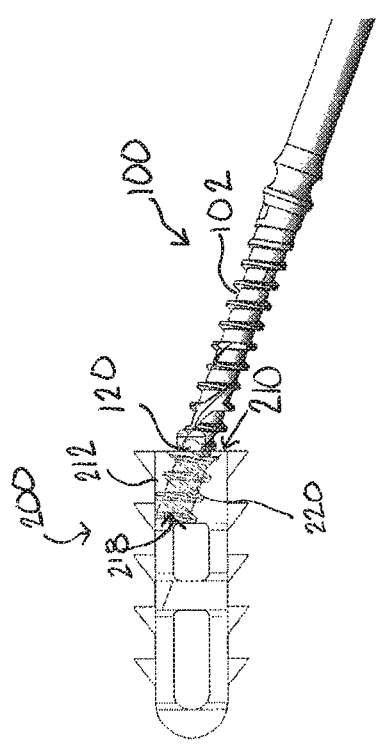
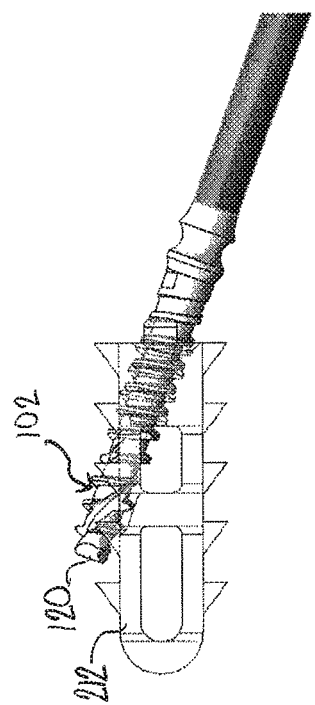
FIG 5A
FIG 5B
FIG 5C
FIG 5D

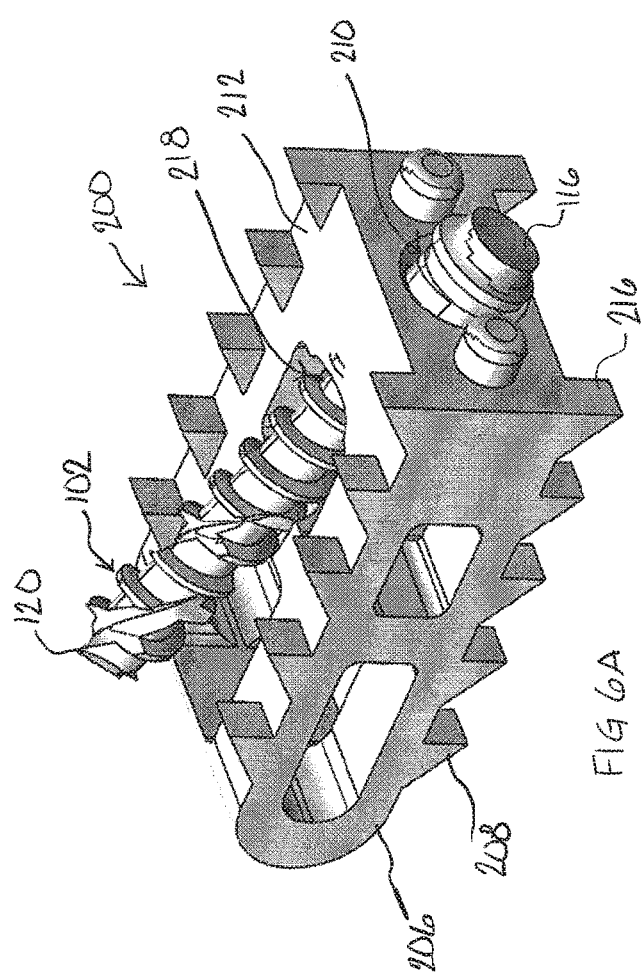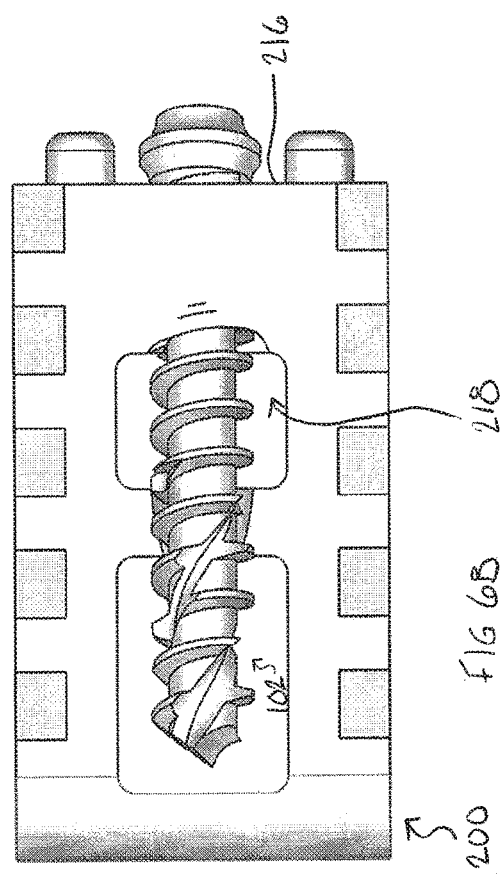

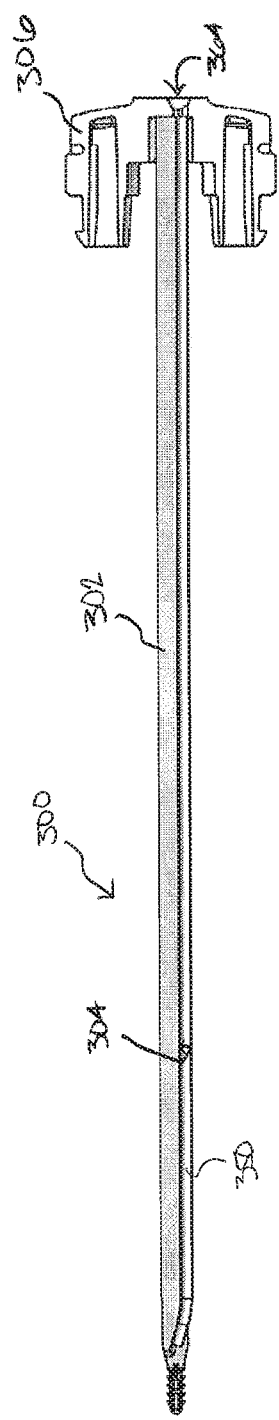
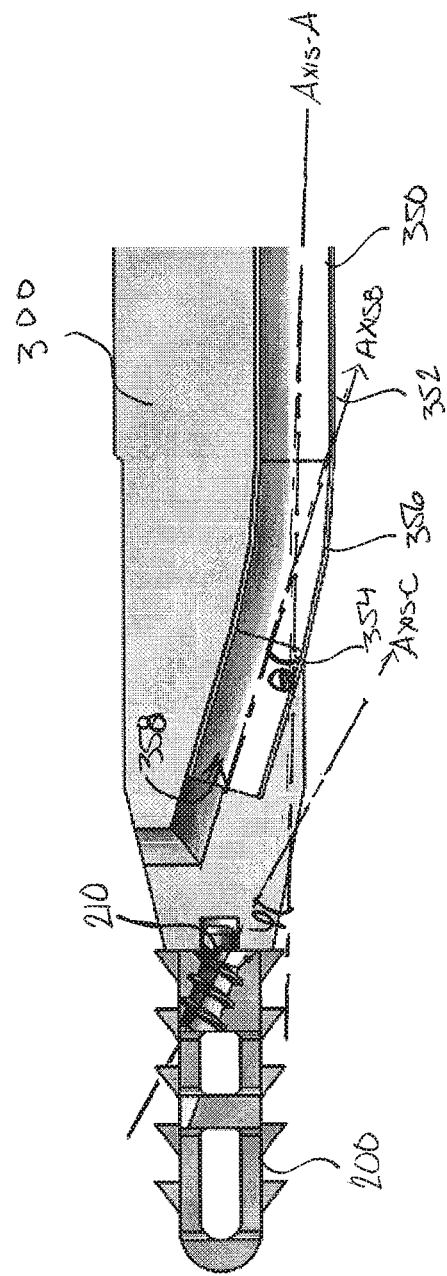
FIG 7A
FIG 7B

METHODS FOR IMPLANTING A BONE SCREW

CROSS-REFERENCE TO RELATED APPLICATION

This application is a continuation of U.S. patent application Ser. No. 14/709,425, filed May 11, 2015 and entitled "METHODS FOR IMPLANTING A BONE SCREW." The entirety of which is hereby incorporated by reference for all purposes.

FIELD

This application is directed to medical devices and methods. More specifically, the application is directed to devices and methods related to use of a bone screw in various spine surgery procedures.

BACKGROUND

Chronic back problems are one of the most common causes of pain and disability in the United States and other developed countries, and they account for enormous economic costs. According to at least one estimate, spinal fusion procedures, in which two adjacent vertebrae are fused together using plates, screws and other implants, are the most commonly performed surgical procedures in the United States. Spinal fusion is often performed in an attempt to increase space between the two adjacent vertebrae being operated on ("spinal distraction") and to thus prevent impingement of the spinal cord or nerve roots branching from the spinal cord and passing through openings in the vertebral column. Unfortunately, most techniques and devices used for performing spinal fusion are relatively invasive and involve a number of risks and difficult recovery and rehabilitation.

One of the reasons that spinal fusion surgery is often very invasive is that, due to the position of the spinal cord in back of (posterior to) the central vertebral bodies of spine, many of the procedures require entering the patient through the front of the body (an "anterior approach") and dissecting through various tissues to gain access to the spine. Fusion procedures are often performed on the cervical spine (neck region), which requires dissecting through the neck, or the lumbar spine (lower back region), which requires dissecting through the abdomen. In either case, cutting through the anterior tissues of the patient to reach the spine is not without risk. Fusion procedures may also involve relatively large plates and screws, which require a relatively large surgical access field and thus more dissection of tissue than would be ideal. Not only are these invasive spinal fusion techniques potentially risky, but they are also expensive and typically require lengthy recovery and rehabilitation times.

Therefore, a need exists for alternative devices and methods for treating spinal stenosis, particularly via fusion of adjacent vertebrae. Ideally, such devices and methods would be minimally invasive or less invasive than many of the currently available techniques. For example, it may be advantageous to have devices and methods that use a posterior approach for accessing the spine. It may also be advantageous to use smaller implants that still achieve a complete fusion. At least some of these objectives will be met by the embodiments described below.

BRIEF SUMMARY

Embodiments described herein address the challenges described above by providing a system for implanting a bone screw through a vertebra of a vertebral column of a patient, the bone screw extending near or through a spinal joint implant in the vertebral column. In some embodiments, the bone screw is advanced through an opening in an implant that has been placed in a facet joint between two vertebrae, so that the bone screw attaches to one of the two vertebrae and thus helps secure the implant in place within the facet joint. In one embodiment, a system for implanting a bone screw includes a bone screw, a bone screw delivery mechanism detachably connected to the bone screw, and a guide tube configured to receive, at a proximal end of the guide tube, the bone screw and bone screw delivery mechanism. The guide tube includes one or more bends, and as the bone screw is advanced through the guide tube along a first trajectory, the bend in the guide tube (or multiple bends) causes the bone screw to exit a distal end of the guide tube along a second trajectory. The angle of the second trajectory is generally configured such that the bone screw enters the vertebra at a desired angle for its intended purpose.

Other embodiments are also described and recited herein. Additionally, the presently disclosed technology is capable of modifications in various aspects, all without departing from the spirit and scope of the invention. Accordingly, the drawings and detailed description are to be regarded as illustrative in nature and not limiting.

In one aspect, a system may be provided, for implanting a bone screw into a vertebra of a vertebral column of a patient to help secure an implant within a joint between the vertebra and an adjacent vertebra. The system may include a bone screw, a bone screw delivery mechanism detachably connected to the bone screw, and a guide tube. The guide tube may include a proximal end, a distal end, a lumen configured to receive the bone screw and the bone screw delivery mechanism, and at least one bend disposed nearer the distal end than the proximal end. The bend (or bends) in the guide tube are designed to change a trajectory of the bone screw and the bone screw delivery mechanism advancing through the lumen from a first trajectory along a longitudinal axis of the guide tube to a second trajectory that is angled relative to the longitudinal axis. The second trajectory is designed to direct the bone screw out of the distal end of the guide tube and into the vertebra at a desired angle to help secure the implant.

In some embodiments, the joint with which the system is used is a facet joint, and the implant is a facet joint implant. In such embodiments, the bone screw, the bone screw delivery mechanism and the guide tube may be designed to advance the bone screw through an opening in the facet joint implant and into the vertebra. In some embodiments, the bend in the guide tube changes the trajectory from the first trajectory to the second trajectory without assistance from a user of the system. In some embodiments, the bone screw delivery mechanism may be detachable from the bone screw by breaking the bone screw delivery mechanism off of the bone screw at a breakable junction. For example, the bone screw delivery mechanism may break off of the bone screw when a predetermined amount of force is applied to the bone screw delivery mechanism and a break in the junction occurs.

In some embodiments, the bone screw delivery mechanism includes a flexible region configured to flex when the delivery mechanism is advanced through the bend in the guide tube. In such embodiments, when the bone screw is engaged with the vertebra and the flexible region is flexed, a load may be concentrated at a breakable junction between the bone screw and the bone screw delivery mechanism. In some embodiments, the bone screw delivery mechanism detaches from the bone screw upon the breakable junction experiencing a predetermined load. Furthermore, in some embodiments, the bone screw and the bone screw delivery mechanism are a one-piece device with a breakable section between the bone screw and the bone screw delivery mechanism. In such embodiments, the bone screw detaches from the bone screw delivery mechanism when the bone screw breaks off of the bone screw delivery mechanism at the breakable section.

In various embodiments, the second trajectory created by the bend (or bends) in the guide tube may be angled between 15 degrees and 55 degrees relative to the longitudinal axis of the guide tube. Optionally, the system may further include an elongate implant delivery device for implanting the implant within the joint. The implant delivery device may have a distal end, a proximal end and a lumen. In such embodiments, the guide tube may be attached to an inner wall of the lumen of the implant delivery device, such that the distal end of the guide tube is disposed at or near the distal end of the implant delivery device. Optionally, the bone screw delivery mechanism may include an elongate shaft and a handle connected to a proximal end of the elongate shaft.

In another aspect, a device for securing a vertebral implant within a joint formed by two adjacent vertebrae may include an elongate bone screw delivery mechanism extending along a longitudinal axis from a proximal end to a distal end and a bone screw detachably connected to the distal end of the bone screw delivery mechanism. In some embodiments, the device may also include a breakable junction between the bone screw delivery mechanism and the bone screw, and the bone screw delivery mechanism is detachable from the bone screw by breaking the bone screw delivery mechanism off of the bone screw at the breakable junction. In some embodiments, the bone screw delivery mechanism breaks off of the bone screw when a predetermined amount of force is applied to the bone screw delivery mechanism and a break in the junction occurs. In some embodiments, the bone screw delivery mechanism includes a flexible region.

The bone screw may include a shaft extending from a screw head, the screw head being monolithically formed with the distal end of the delivery mechanism. In some embodiments, for example, the shaft extends from the screw head along the longitudinal axis. In some embodiments, the bone screw and the bone screw delivery mechanism are a one-piece device with a breakable section between the bone screw and the bone screw delivery mechanism.

In another aspect, a system for securing a facet joint implant to a vertebra may include a one-piece bone screw device and a guide tube. The one-piece bone screw device may include a proximal elongate shaft portion, a distal bone screw portion, and a breakable junction between a distal end of the proximal elongate shaft portion and a proximal end of the distal bone screw portion that is designed to break when a sufficient amount of force is applied to the bone screw device while screwing the distal bone screw portion into the vertebra. The guide tube may include a proximal end, a distal end, a lumen configured to receive the bone screw device, and a bend disposed nearer the distal end than the proximal end. The bend in the guide tube is designed to change a trajectory of the bone screw device advancing through the lumen from a first trajectory along a longitudinal axis of the guide tube to a second trajectory that is angled relative to the longitudinal axis. The second trajectory is configured to direct the distal bone screw portion out of the distal end of the guide tube and into the vertebra at a desired angle.

In some embodiments, the second trajectory is configured to direct the distal bone screw portion through an opening in the facet joint implant and thus into the vertebra. In some embodiments, the proximal elongate shaft portion includes a flexible region configured to flex when the bone screw device is advanced through the bend in the guide tube. In some embodiments, when the distal bone screw portion is engaged with the vertebra and the flexible region is flexed, a load is concentrated at the breakable junction. In some embodiments, the distal bone screw portion breaks off of the proximal elongate shaft portion at the breakable junction when the breakable junction experiences a predetermined load.

In various embodiments, the second trajectory may be angled between 15 degrees and 55 degrees relative to the longitudinal axis of the guide tube. In some embodiments, the system may include an elongate implant delivery device for implanting the implant within a facet joint formed by the vertebra and an adjacent vertebra. The implant delivery device have a distal end, a proximal end and a lumen. The guide tube may be attached to an inner wall of the lumen of the implant delivery device, such that the distal end of the guide tube is disposed at or near the distal end of the implant delivery device. Optionally, the bone screw device may further include a handle coupled with a proximal end of the proximal elongate shaft portion.

In another aspect, a method for implanting a bone screw in a vertebra may involve inserting the bone screw and a bone screw delivery mechanism through a proximal end of a guide tube along a first trajectory, where a proximal end of the bone screw is attached to a distal end of the bone screw delivery mechanism, and a distal end of the guide tube is positioned adjacent the vertebra. The method may further involved advancing the bone screw and the bone screw delivery mechanism through a bend in the guide tube to cause the bone screw to exit the distal end of the guide tube along a second trajectory and contact the vertebra. The method may also involve rotating the delivery mechanism to cause the bone screw to screw into the vertebra and detaching the bone screw delivery mechanism from the bone screw.

In some embodiments, the bone screw delivery mechanism is advanced through the guide tube in a straight direction along the first trajectory, and the bend in the guide tube automatically adjusts a path of travel of the bone screw delivery mechanism from the first trajectory to the second trajectory. In some embodiments, detaching the bone screw delivery mechanism from the bone screw comprises breaking the bone screw delivery mechanism off of the bone screw at a breakable junction. For example, breaking the bone screw delivery mechanism off of the bone screw may involve screwing the bone screw into the vertebra until a break in the junction occurs. More generally, breaking the bone screw delivery mechanism off of the bone screw may involve applying force to the bone screw delivery mechanism until a break in the junction occurs. In some embodiments, the bone screw and the bone screw delivery mechanism are a one-piece device with a breakable section between the bone screw and the bone screw delivery mechanism. In such embodiments, detaching the bone screw delivery mechanism from the bone screw may involve breaking the bone screw delivery mechanism off of the bone screw at the breakable section.

In various embodiments, the first trajectory extends along a longitudinal axis of the guide tube, and the second trajectory is angled between 15 and 55 degrees relative to the longitudinal axis. The method may further involve advancing the guide tube into the patient to position the distal end of the guide tube adjacent the vertebra. In some embodiments, this advancing of the guide tube involves advancing it through a larger guide tube previously placed in the patient proximate the vertebra.

In some embodiments, the step of advancing the bone screw may involve advancing the bone screw through an opening in a facet joint implant located in a facet joint formed by the vertebra and an adjacent vertebra. Optionally, the method may further involve, prior to the inserting step: advancing a larger guide tube into the patient from a posterior approach, to position a distal end of the larger guide tube in the facet joint; implanting the facet joint implant in the facet joint through the larger guide tube; and positioning the guide tube in a desired position for advancing the bone screw through the facet joint implant. In some embodiments, when the bone screw is engaged with the vertebra and the flexible region is flexed, a load is concentrated at a breakable junction. In some embodiments, the bone screw delivery mechanism detaches from the bone screw upon the breakable junction experiencing a predetermined load.

In another aspect, a method for implanting a bone screw through a facet joint implant to attach to a vertebra may involve: advancing a guide tube into the patient to position a distal end of the guide tube adjacent the facet joint; inserting a distal end of a bone screw device through the guide tube along a first trajectory; advancing the bone screw device through a bend in the guide tube to cause a distal bone screw portion of the bone screw device to exit the distal end of the guide tube along a second trajectory and advance through an opening in the facet implant at an angle; rotating the bone screw device to cause the distal bone screw portion to screw into the vertebra to secure the facet joint implant to the vertebra; and breaking a proximal elongate shaft portion of the bone screw device off of the distal bone screw portion at a breakable junction between the two portions.

Advancing the bone screw device may involve advancing the bone screw device in a straight direction along the first trajectory, where the bend in the guide tube automatically adjusts a path of travel of the bone screw device from the first trajectory to the second trajectory. In some embodiments, breaking the proximal elongate shaft portion off of the distal bone screw portion involves screwing the distal bone screw portion into the vertebra until a break in the breakable junction occurs. In other embodiments, breaking the proximal elongate shaft portion off of the distal bone screw portion comprises applying force to the proximal elongate shaft portion until a break in the breakable junction occurs. In some embodiments, the proximal elongate shaft portion and the distal bone screw portion are a one-piece device with the breakable junction between them.

In another aspect, a is provided for method for implanting a bone screw in a vertebra at or immediately adjacent a spinal joint implant disposed in a spinal joint formed by the vertebra and an adjacent vertebra. The method may first involve inserting a bone screw delivery mechanism through a proximal end of a guide tube along a first trajectory, where a distal end of the bone screw delivery mechanism is attached to a proximal end of the bone screw, and where a distal end of the guide tube is positioned proximate the spinal implant. The method may next involve advancing the bone screw delivery mechanism through one or more bends in the guide tube to cause the bone screw to exit the distal end of the guide tube along a second trajectory and contact the vertebra. The method may further involve rotating the delivery mechanism to cause the bone screw to screw into the vertebra to help secure the spinal joint implant within the spinal joint and separating the bone screw delivery mechanism from the bone screw.

In some embodiments, the bone screw may be advanced through an opening in the spinal joint implant to contact the vertebra. In some embodiments, the spinal joint is a facet joint, and the spinal joint implant is a facet joint implant. In some embodiments in which the spinal joint is a facet joint and the spinal joint implant is a facet joint implant, the bone screw may be advanced into the vertebra immediately posterior to a posterior end of the facet joint implant, to help prevent the facet joint implant from backing out of the facet joint.

In some embodiments, separating the bone screw delivery mechanism from the bone screw involves separating the bone screw delivery mechanism off of the bone screw at a junction. In some embodiments, separating the bone screw delivery mechanism off of the bone screw may involve screwing the bone screw into the vertebra until a break in the junction occurs. In some embodiments, separating the bone screw delivery mechanism off of the bone screw comprises applying force to the bone screw delivery mechanism until a break in the junction occurs.

In some embodiments, the first trajectory extends along a longitudinal axis of the guide tube, and the second trajectory is angled between 15 and 55 degrees relative to the longitudinal axis. Optionally, the method may further involve advancing the guide tube into the patient to position the distal end of the guide tube proximate to the spinal joint. Such embodiments may also involve advancing the guide tube through a larger guide tube previously placed in the patient proximate the spinal joint.

These and other aspects and embodiments will be described in further detail below, in reference to the attached drawing figures.

BRIEF DESCRIPTION OF DRAWINGS

FIG. 1 is a perspective view of a bone screw device, including a bone screw and a bone screw delivery mechanism, according to certain embodiments;

FIG. 2 is a detailed perspective view of a distal end of the bone screw device of FIG. 1, according to certain embodiments;

FIGS. 5A-5D are side views of the bone screw device of FIG. 1, as it is inserted into a facet joint implant, according to certain embodiments;

FIGS. 6A-6B are perspective and top views of the bone screw of FIG. 1, with the bone screw inserted into the facet joint implant and detached from the bone screw delivery mechanism, according to certain embodiments;

FIG. 7A is a side view of an implant delivery device and a facet joint implant, according to certain embodiments;

FIG. 7B is a detailed side view of the implant delivery device and implant of FIG. 7A, according to certain embodiments;

DETAILED DESCRIPTION

Figure 3:
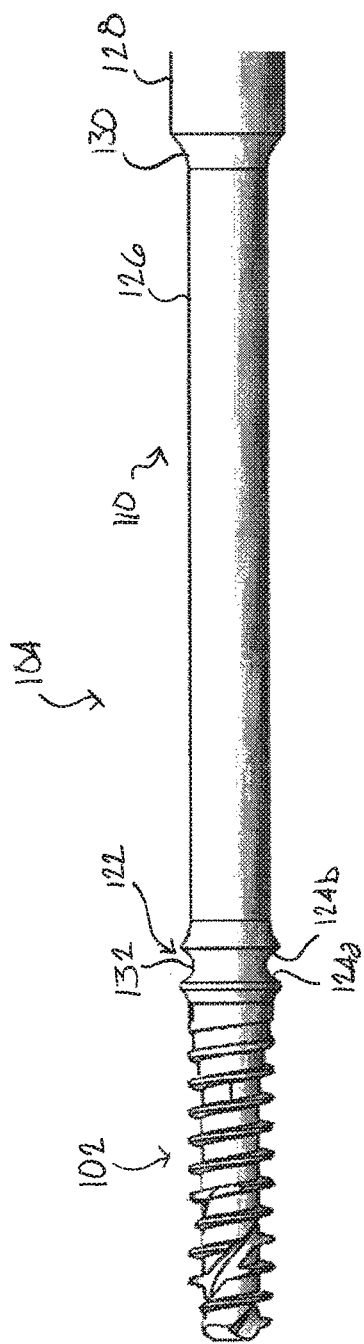
FIG. 3 is a side view of the bone screw device of FIG. 1, according to certain embodiments.

Aspects of the present disclosure generally involve devices and methods for treating spinal stenosis. Spinal stenosis reflects a narrowing of one or more areas of the spine, often in the upper or lower back. This narrowing can put pressure on the spinal cord or on the nerves that branch out from the compressed areas. Individual vertebrae of the spine are positioned relative to each other, and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

Various embodiments of a device, system and method are described herein for distracting two adjacent vertebrae of a spine, in an effort to ameliorate spinal stenosis. Some embodiments involve distracting a facet joint from a posterior approach. Distracting one or both facet joints between two adjacent vertebrae may be effective in treating spinal stenosis and possibly other nerve impingement conditions. Due to the location and small size of the facet joints, these joints may be distracted using (1) significantly smaller implants than are required for distracting the central vertebral bodies and (2) a posterior surgical approach to the spine. For these reasons, facet joint distraction may be significantly less invasive but still very effective compared to other methods used for spinal distraction.

In many cases, it may be possible to insert a facet joint implant into a facet joint by itself and, due to the design of the implant, do nothing further to secure the implant within the joint. In other words, the shape, size, surface features and overall configuration of the implant may cause it to remain securely within the facet joint without further attachment devices required. In some cases however, and in general for overall safety of a facet joint distraction procedure, it may be advantageous to use one or more additional devices to help secure the facet joint implant to one or both of the adjacent vertebrae that form the joint. Such an additional device may include a screw, anchor, or similar securement device, and it may help to maintain the implant in a desired position within the joint and to prevent it from "backing out" of the joint—i.e., slipping posteriorly out of the joint. In such embodiments, a bone screw may be delivered through an opening in a facet joint implant or adjacent the facet joint implant, so that the screw is attached to one of the vertebrae that form the facet joint, to help secure the implant within the joint. In other embodiments, which will not be described herein, a bone screw may be used without an additional implant and may thus act as the distraction device itself. In yet other embodiments, the bone screw may be implanted in central vertebral body of a vertebra. Thus, although this detailed description focuses on embodiments in which the bone screw is advanced through an opening in a facet joint implant to secure the implant in a facet joint, alternative embodiments may use the bone screw system, device and method in other ways within the spine. For example, in some embodiments, the bone screw may be advanced through an opening in an implant to secure the implant to a different spinal joint besides a facet joint. In some embodiments, the bone screw may be secured to a vertebra adjacent a facet or other spinal joint implant (bot not through the implant), to help prevent the implant from slipping posteriorly out of the spinal joint.

In one embodiment, a bone screw system may include a bone screw device and an implant delivery device for anchoring an implant into a facet joint, and for distracting and maintaining the distracted position of the joint. In one embodiment, the bone screw device may include a bone screw that is detachably connected to a bone screw delivery mechanism. The implant delivery device may be configured to cause the bone screw to detach from the delivery mechanism upon the bone screw becoming sufficiently secured to the implant and facet joint. This approach may ensure that the implant is securely affixed to the facet joint, for maintaining the distraction of the joint, thereby relieving symptoms associated with spinal stenosis.

In one particular aspect, the system includes a bone screw detachably connected to a delivery mechanism at a breakable junction, and a guide tube configured to receive the bone screw and delivery mechanism. The guide tube may include a bend, and as the bone screw is advanced through the guide tube along a first trajectory, the bend causes the bone screw to exit a distal end of the guide tube along a second trajectory. The delivery mechanism may include a flexible region, which flexes as it advances through the bend in the guide tube. In some embodiments, the guide tube may include multiple bends. The bend (or bends) in the guide tube are configured to direct the bone screw out of the distal end of the guide tube at a desired angle, such as an angle that will direct the bone screw through an opening in a spinal joint implant and into one of two adjacent vertebrae. As the bone screw is screwed into vertebral bone, the flexible region of the delivery mechanism continues to flex, and a load is concentrated at the breakable junction. Upon the bone screw becoming sufficiently secured to the vertebral bone, the breakable junction experiences a predetermined load to cause the bone screw to detach from the delivery mechanism.

FIG. 1 shows a perspective view of a bone screw device 100, including a bone screw 102 and a bone screw delivery mechanism 104, according to certain embodiments. The bone screw 102 is detachably connected to the delivery mechanism 104. In some embodiments, the bone screw 102 and delivery mechanism 104 are separate components that couple together for delivery of the bone screw 102 and then separate when the bone screw 102 is secured to a vertebra, similar to the way a conventional screw and screwdriver work. In other embodiments, the bone screw 102 and delivery mechanism 104 are separate components, which are attached to one another at a breakable junction during manufacturing, and the breakable junction is configured to break upon experiencing a predetermined load. In yet other embodiments, the bone screw 102 and delivery mechanism 104 are manufactured as a one-piece, monolithically formed unit, having a breakable junction, which breaks upon experiencing a predetermined load. Therefore, although the following description focuses on the embodiment in which the bone screw 102 and the delivery mechanism 104 are a one-piece unit, other embodiments are possible and are encompassed within the scope of the disclosure.

The bone screw device 100 may extend longitudinally from a proximal end 106 to a distal end 108 along Axis-I. In some embodiments, the bone screw device 100 may include a holding portion or a handle 112. The bone screw delivery mechanism 104 may include an elongate shaft 110, extending from a proximal end, where it attaches to or includes the handle 112, to a distal end where it is joined to the bone screw 102. The elongate shaft 110 of the delivery mechanism 104 may include a proximal region 128 that tapers (at 130) to a flexible region 126, which may facilitate the bone screw 102 in detaching from the delivery mechanism 104, the details of which will be described in further detail below.

FIG. 2 shows a detailed perspective view of a distal portion of the bone screw device 100 of FIG. 1, according to certain embodiments. As shown, the bone screw 102 may comprise a tip 120, a helical ridge 114, and a groove 118. The bone screw 102 may screw into a facet joint implant (or other spinal implant) and a vertebra, to secure the implant in the joint and thus prevent the implant from backing out of the joint. The delivery mechanism 104 may be used to insert and secure the bone screw 102 to the vertebral bone. The bone screw device 100 may be configured such that, upon securing the bone screw 102 into the implant and the vertebra, the bone screw 102 may detach from the delivery mechanism 104. As such, the bone screw 102 may be inserted and secured into the vertebra and the facet joint implant with minimal invasiveness.

Referring to FIGS. 2 and 3, the bone screw 102 may be detachably connected to the delivery mechanism 104 at a breakable junction 122. The breakable junction may include a distal portion 124a and a proximal portion 124b that taper to form an arcuate shaped groove 132. The groove 132 may break upon experiencing a predetermined amount of force, the details of which will be described in detail below.

Figure 4:
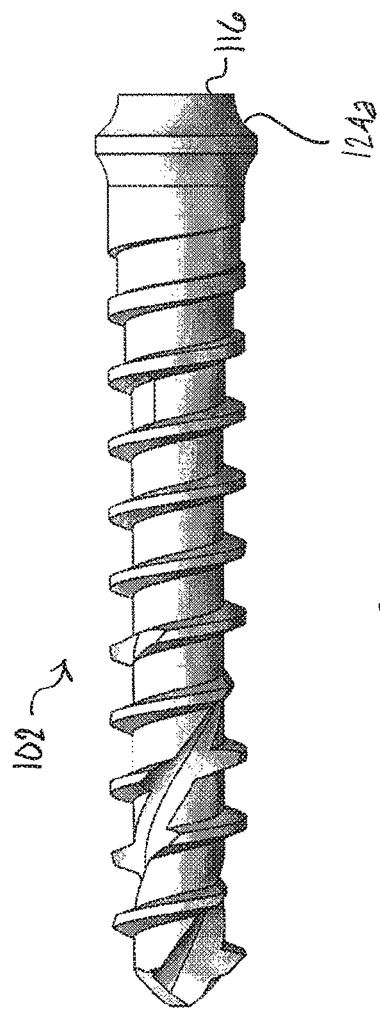
FIG. 4 is a side view of the bone screw of FIG. 1, after it has been detached from the bone screw delivery mechanism of FIG. 1, according to certain embodiments.
Figure 8A:
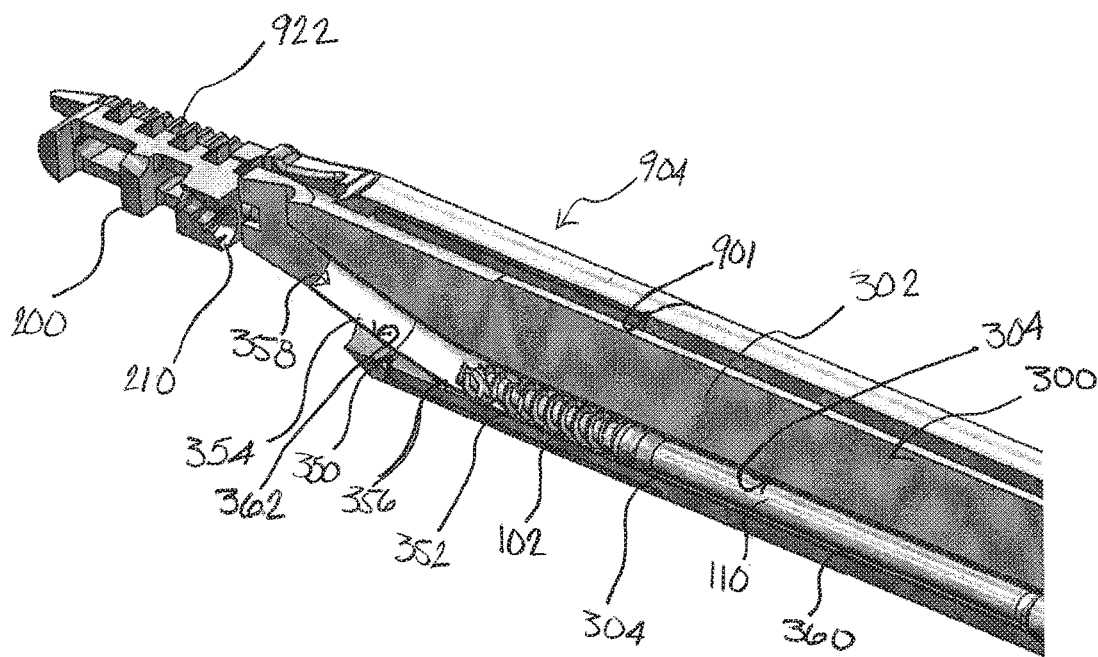
FIGS. 8A-8D are perspective and side views, respectively, of the bone screw device of FIG. 1, inserted within the implant delivery device of FIGS. 7A-7B and proximate a facet joint implant, according to certain embodiments.
Figure 8B:
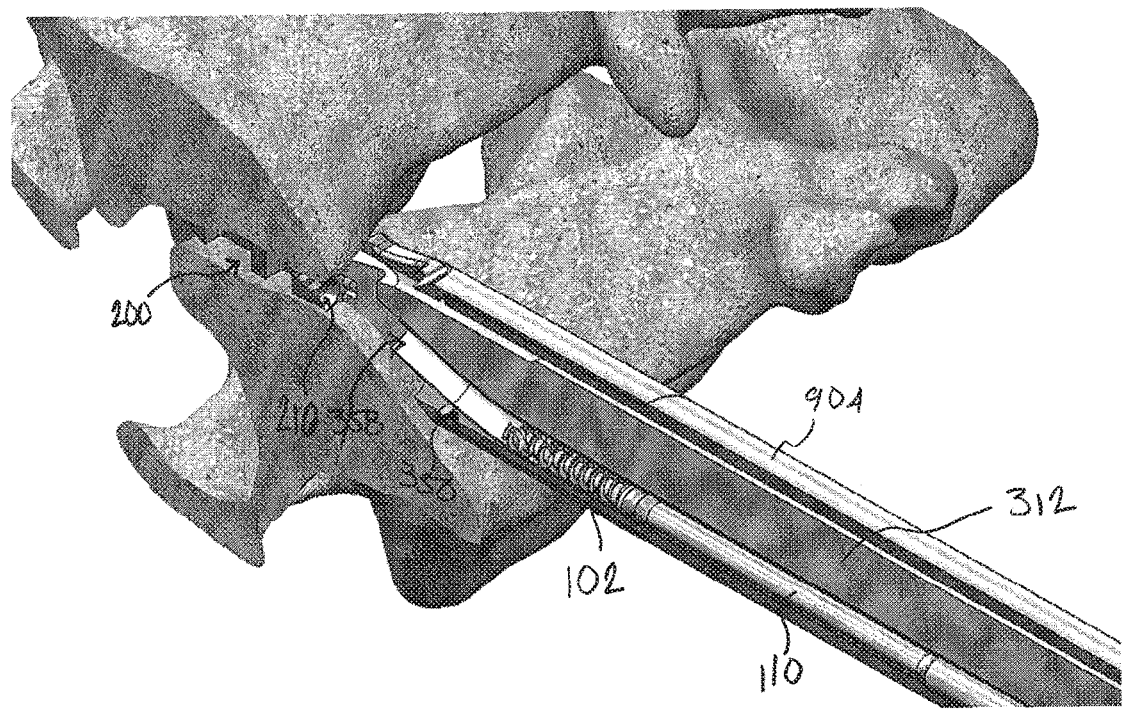
Figure 8C:
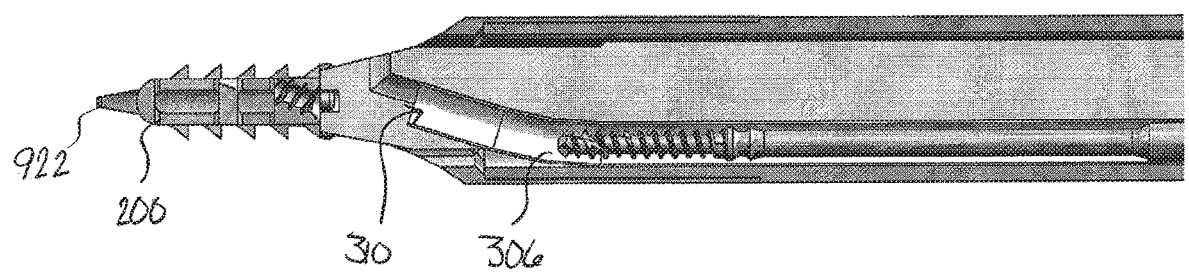
Figure 8D:
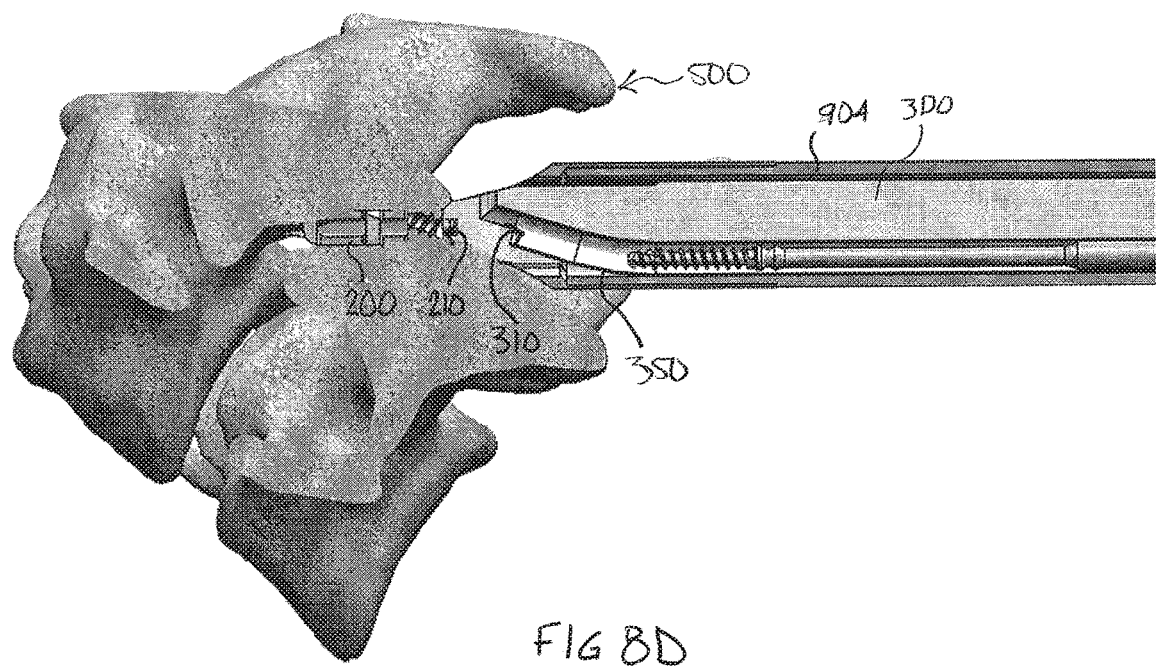

As shown in FIG. 4, upon the breakable junction 122 breaking, the bone screw 102 may detach from the delivery mechanism 104, so that a screw head 116 is exposed. The delivery mechanism 104 may be removed, and the bone screw 102 may remain attached to the vertebra, to help anchor the implant within the facet joint.

FIGS. 5A-5D show side views of the bone screw device 100 of FIG. 1, as the bone screw 102 is inserted into a facet joint implant 200 and a vertebra, according to certain embodiments. While the illustrated embodiment involves inserting the bone screw 102 through the facet joint implant 200, in some embodiments, the bone screw 102 may be inserted near, but not into, the implant 200. For example, the bone screw 102 may be inserted directly into a vertebra and behind the implant 200, to prevent the implant 200 from backing out of the joint.

The depicted facet joint implant 200 is exemplary, and in alternative embodiments the bone screw device 100 may be used to secure any suitable implant within a vertebral joint. In the depicted embodiment, the implant 200 may include a top wall 212, a bottom wall 216, and an inlet 210 extending therebetween. The inlet 210 may lead to a screw cavity 220, which leads to an outlet 218. The outlet 218 may be located within the top wall 212 so that the screw 102 may screw into the upper vertebra of a patient's facet joint to secure the implant 200 thereto. The screw cavity 220 may include female threads configured to engage with the helical ridge 114 of the bone screw 102. Thus, when securing the bone screw 102 to the implant 200, a user may rotate the bone screw device 100 to cause the helical ridge 114 to mate with the female threads within the screw cavity 220 so that the screw 102 progresses through the cavity 220. FIGS. 5A-5D show the bone screw 102 progressing through the inlet 210 and out the outlet 218. When the bone screw 102 is sufficiently screwed into implant 200 and vertebra to secure the implant 200 to the vertebra, the bone screw 102 may detach from the delivery mechanism 104.

FIGS. 6A-6B show the bone screw 102 secured to the implant 200 after the bone screw 102 has detached from the delivery mechanism 104. According to certain embodiments, the implant 200 may include a textured surface that provides friction between the facet joint and the implant 200. For example, at least one of the top wall 212 or the bottom wall 216 may include ridges 206 extending generally perpendicularly from the walls 212, 216 and/or along the length of the implant 200. In some implementations, the implant 200 may be entirely formed by bone or bone substitute material, although this disclosure is in no way limited thereto.

Now turning to FIGS. 7A-12, disclosed herein is an implant delivery device 300 for deploying the bone screw device 100. More particularly, the implant delivery device 300 may be used with the bone screw device 100 and configured to cause the bone screw 102 to detach from the delivery mechanism 104 upon the bone screw 102 becoming sufficiently secured to the implant 200 and vertebra. In some embodiments, upon the bone screw 102 being sufficiently screwed into the vertebra, the delivery device 300 may cause a predetermined amount of force to be exerted on the breakable junction 122 of the bone screw device 100. For example, the delivery device 300 may be configured to cause the flexible region 126 of the delivery mechanism 104 to flex as the screw 102 is screwed into the implant 200. The flexible region 126 may flex as part of, or independently of, the bone screw 102. In embodiments in which the bone screw 102 and delivery mechanism 104 are separate components, the bone screw 102 may bend and/or change its trajectory at the junction. When the screw 102 is screwed into the implant 200 a predetermined amount, the delivery device 300 may cause the flexible region 126 to sufficiently flex to exert a predetermined amount of force on the breakable junction 122 and thereby break the breakable junction 122. As such, the bone screw 102 may be delivered to secure the implant 200 into a patient's spinal joint in a minimally invasive manner.

As shown in FIG. 7A, the implant delivery device 300 may include a shaft 302 with a lumen 304 extending therethrough. In some embodiments, the delivery device 300 may include a handle 306 for engaging with other components of a deployment system, the details of which will be described in further detail below. The delivery device 300 may include an inner guide tube 350 extending within the lumen 304.

The inner guide tube 350 may be configured to receive the bone screw device 100 and guide the bone screw 102 to the implant 200. For example, when the implant delivery device 300 is used with a guide tool 904 (which will be explained in detail with reference to FIGS. 13-21B below), the outlet 358 of the inner guide tube 350 may align with the facet implant inlet 210. Thus, as the bone screw device 100 is advanced through the inner guide tube 350, the bone screw 102 may exit the outlet 358 and engage (e.g., catch onto) the implant inlet 210. A user may then continue to advance the bone screw 102 through the implant 200 by rotating the bone screw device 100, and thus cause the screw 102 to screw into the implant 200 and into the patient's vertebra. The inner guide tube 350 may include a proximal portion 352 that extends longitudinally along Axis-A and a distal portion 354 that extends along Axis-B, wherein the proximal portion 352 and distal portion 354 are joined at a bend 356. Axis-B may extend upward from Axis-A at an angle θ, measured from the distal end. Angle θ may be, for example, between 5° and 35°. In some embodiments, angle θ may be between 10° and 25°. As shown in FIG. 7B, the screw cavity 220 of the facet joint implant 200 may extend from the inlet 210 to the outlet 218 at an angle. For example, when the implant delivery device 300 is engaging the implant 200 (as shown in FIG. 7B), the cavity 220 may extend upward from Axis-A at an angle φ, measured from the distal end. Angle φ may be slightly greater than angle θ. Angle φ may be, for example, between 5° and 35°. In some embodiments, angle φ may be between 10° and 25°. The angle of the bend θ, together with the angle of the screw cavity φ, may be configured to cause the bone screw 102 to detach from the delivery mechanism 104 upon securing the implant 200 to a vertebra 500 of a patient's facet joint. As the bone screw 102 is advanced through the inner guide tube 350, the bend 356 in the inner guide tube 350 may be configured to cause the flexible region 126 of the delivery mechanism 104 to flex. When the bone screw 102 is screwed into the implant 200 and vertebra a predetermined amount (e.g., to fully secure the implant 200 into the vertebra), the bone screw 102 may become stabilized so that the flexing or bending force is concentrated at the breakable junction 122. As such, when a user further secures the screw 102, the force on the breakable junction reaches a threshold and causes the junction 122 to break, thus detaching the bone screw 102 from the delivery mechanism 104. Thus, the implant delivery device 300 may facilitate a user in securing the bone screw 102 into an implant 200 and vertebra a sufficient amount and in a minimally invasive manner.

FIGS. 8A-8D show perspective and side views of the bone screw device 100 that is inserted into the implant delivery device 300, according to certain embodiments. FIGS. 8A-8D show a stage in the securing process in which the bone screw 102 is still within the proximal portion 352 of the inner guide tube 350 (e.g., the bone screw 102 has not yet entered the distal portion 354 of the inner guide tube 350), and thus the inner guide tube 350 has not yet caused the flexible region 126 of the delivery mechanism 104 to flex. As shown, the bone screw 102 is traveling along a first trajectory (e.g., along Axis-A, as shown in FIG. 7B).

Figure 9A:
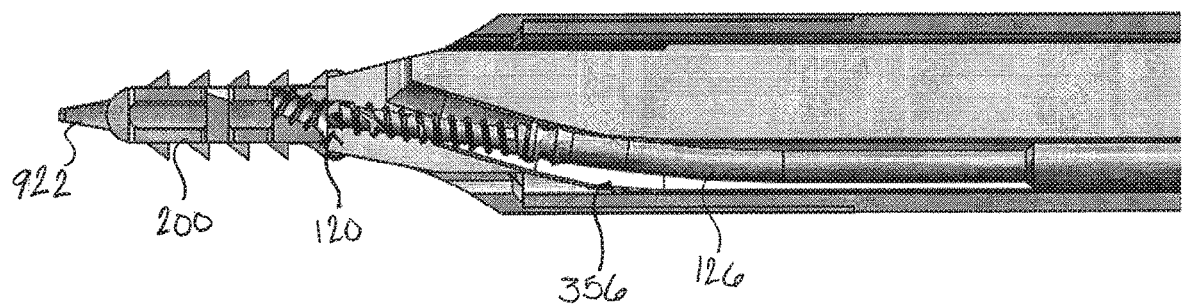
FIGS. 9A-9B are side views of the bone screw device of FIG. 1, further inserted within the implant delivery device of FIGS. 7A-7B and engaging the facet joint implant, according to certain embodiments.
Figure 9B:
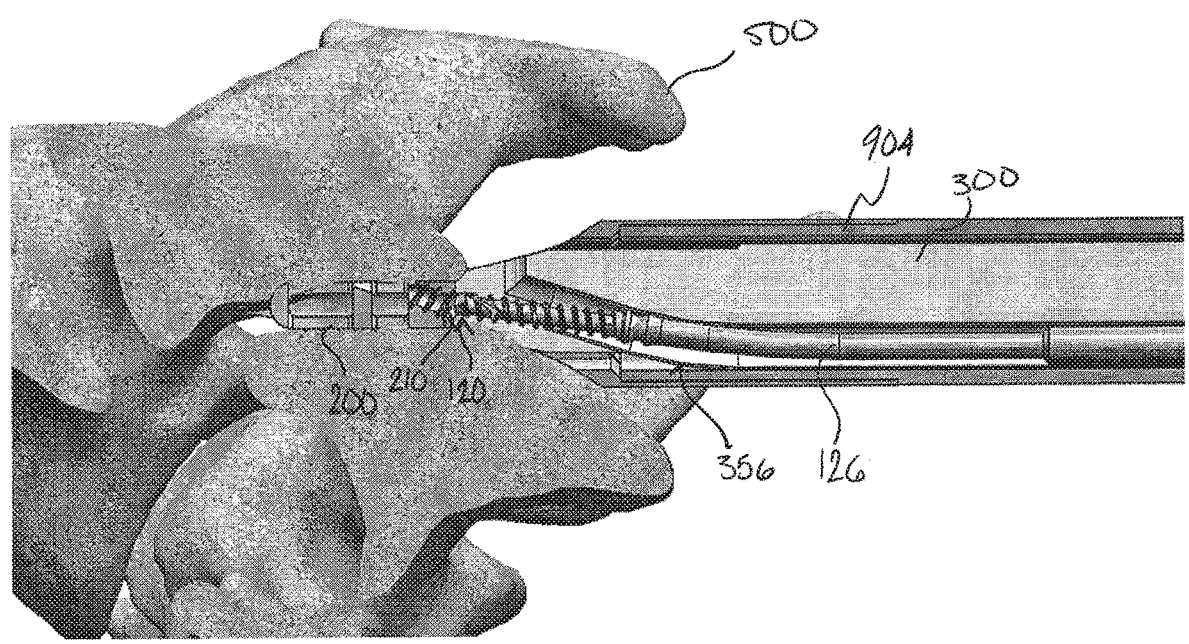

FIGS. 9A-9B show side views of the bone screw device 100 further inserted into the implant delivery device 300 of FIGS. 8A-8D and entering into the facet joint implant 200, according to certain embodiments. FIGS. 9A-9B show a stage in the securing process in which the tip 120 of the bone screw 102 has engaged the inlet 210 of the facet implant 200, and the flexible region 126 of the delivery mechanism 104 is within the bend 356 of the inner guide tube 350 and thus flexes. As shown, the bone screw 102 is traveling along a second trajectory (e.g., along Axis-B, as shown in FIG. 7B) through the inner guide tube outlet 358.

Figure 10A:
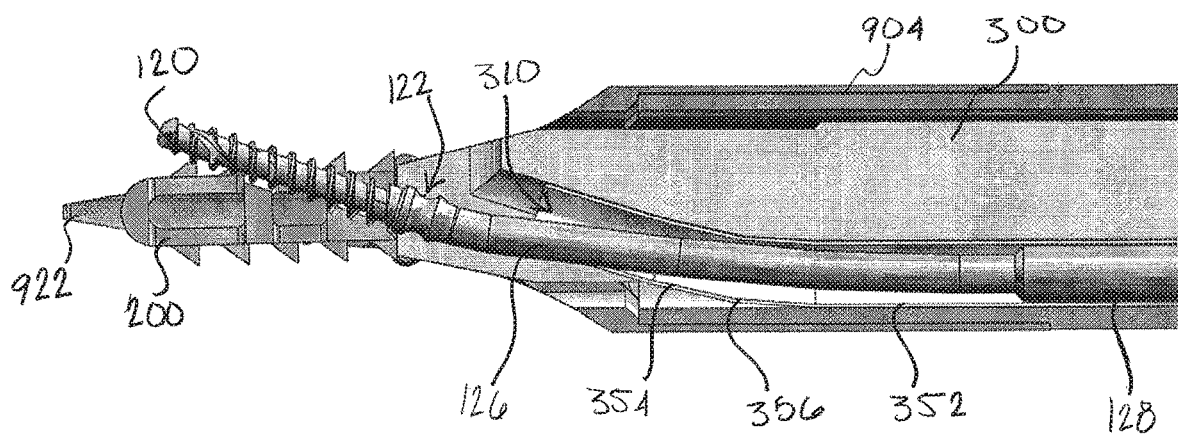
FIGS. 10A-10B are side views of the bone screw device of FIG. 1 even further inserted into the implant delivery device of FIGS. 7A-7B, with the bone screw further engaging the facet joint implant, according to certain embodiments.
Figure 10B:
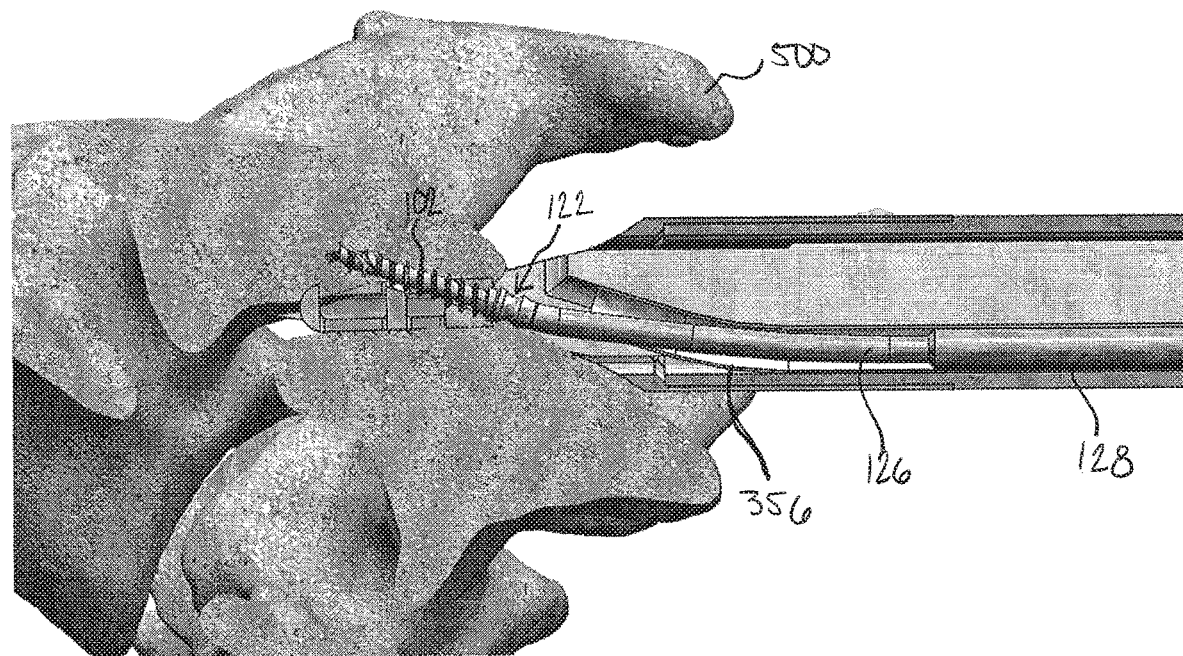

FIGS. 10A-10B show side views of the bone screw device 100 even further inserted into the implant delivery device 300 of FIGS. 8A-8D, with the bone screw inserted within the facet joint implant 200, according to certain embodiments. FIGS. 10A-10B show a stage in the securing process in which the bone screw 102 is threadedly engaging the facet implant 200, and the flexible region 126 of the delivery mechanism 104 further flexes. As shown, the bone screw 102 is traveling along a third trajectory (e.g., along Axis-C, as shown in FIG. 7B) through the screw cavity 220.

Figure 11A:
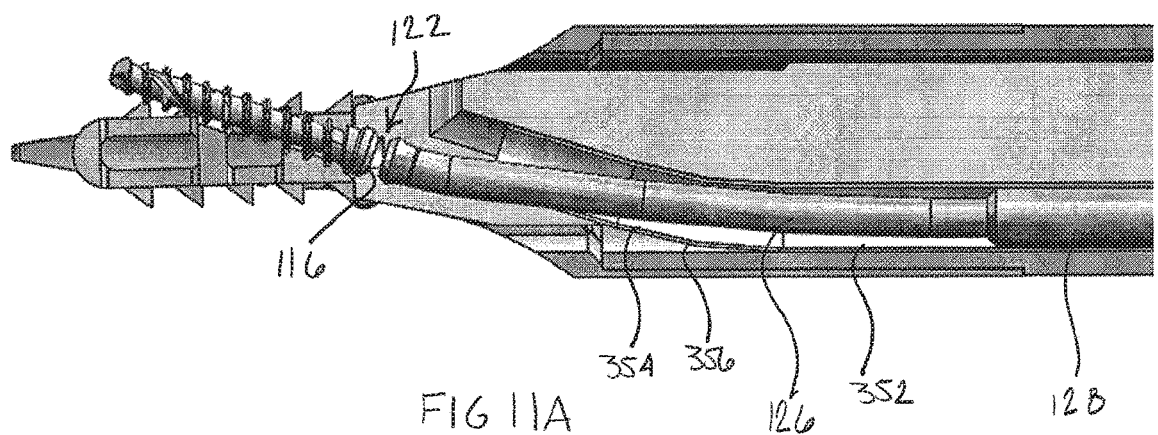
FIGS. 11A-11B are side views of the bone screw device of FIG. 1, secured to the facet joint implant and detached from the bone screw delivery mechanism, according to certain embodiments.
Figure 11B:
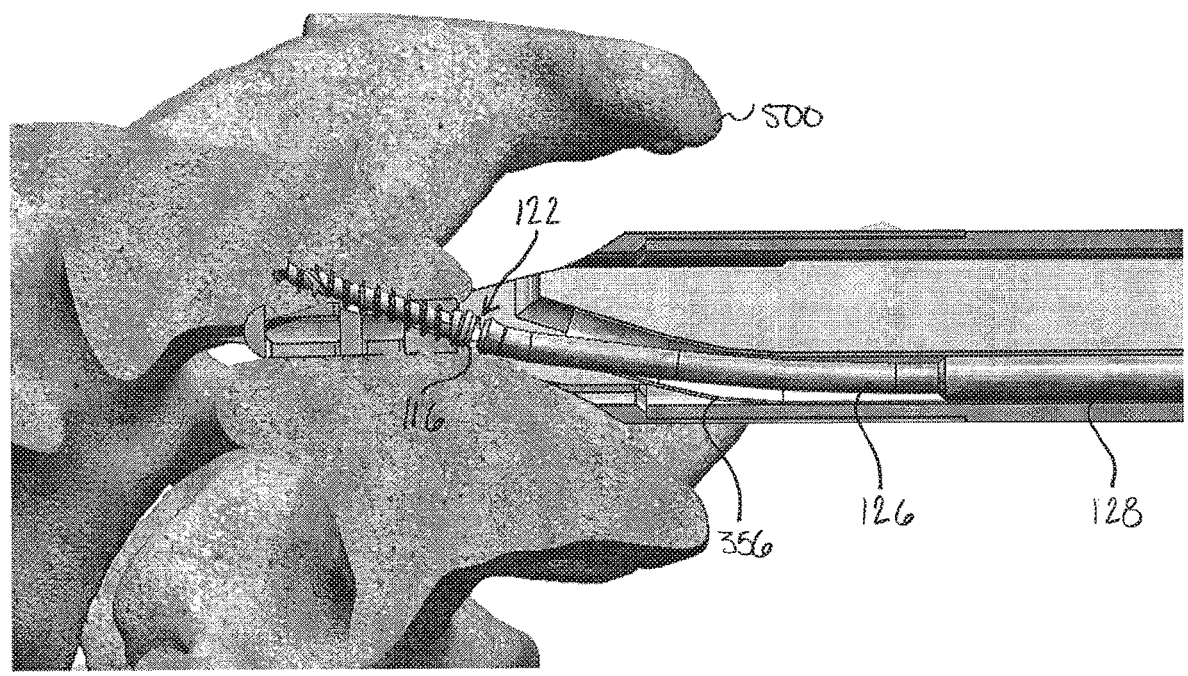
Figure 12:
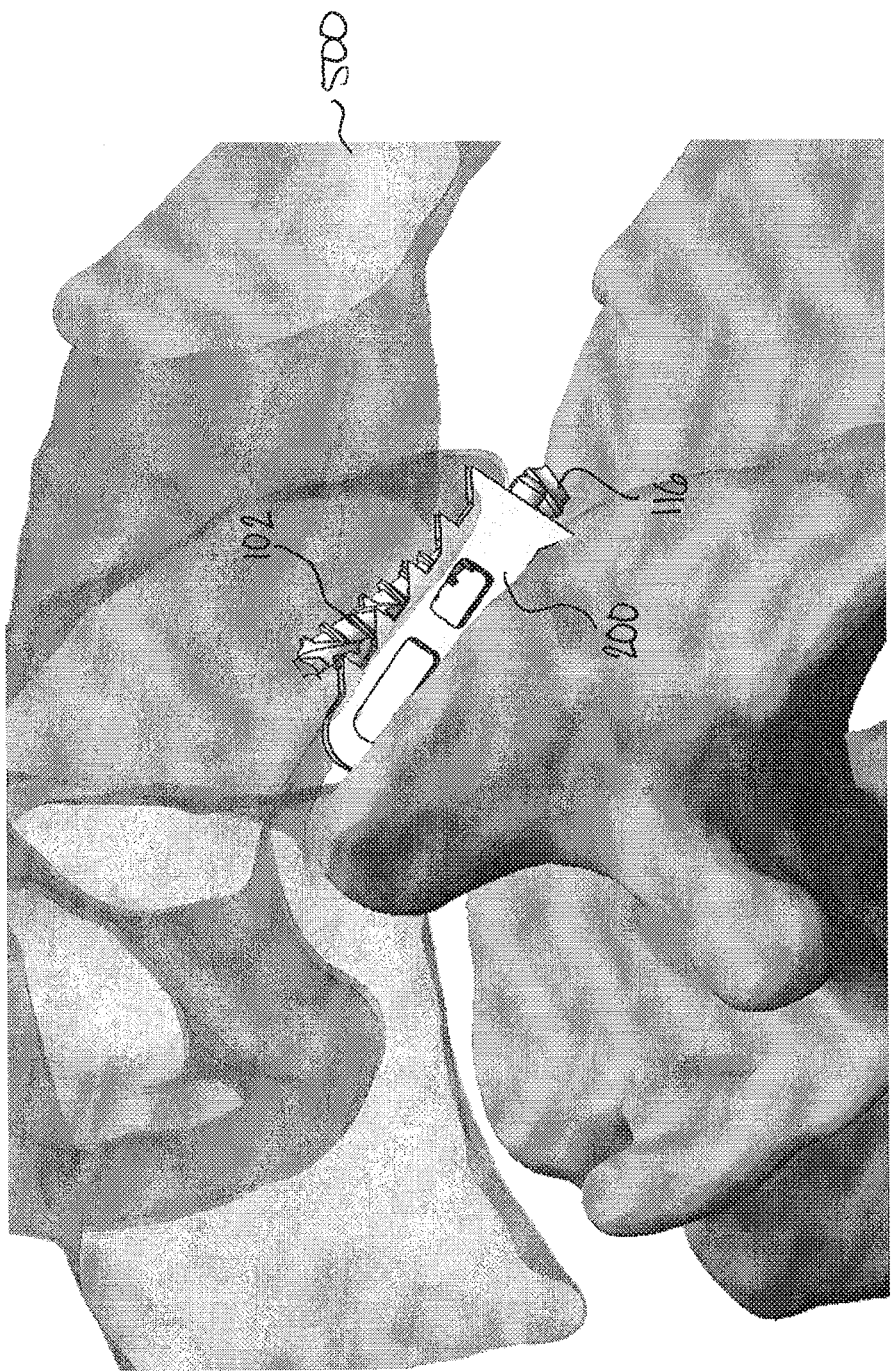
FIG. 12 is a perspective view of the bone screw of FIG. 1, anchoring a facet joint implant to a facet joint of vertebral column of a patient, according to certain embodiments.

FIGS. 11A-11B show side views of the bone screw device 100 within the implant delivery device 300 of FIGS. 8A-8D, with the bone screw 102 secured to the facet joint implant 200 and detached from the bone screw delivery mechanism 104, according to certain embodiments. FIGS. 11A-11B show a stage in the securing process in which the bone screw 102 is sufficiently secured to the facet implant 200 and the upper vertebra 500 of the facet joint. The flexible region 126 of the delivery mechanism 104 has bent sufficiently far so that the load concentrated at the breakable junction 122 has reached a predetermined threshold, causing the breakable junction 122 to break. Thus, the delivery mechanism 104 has become detached from the bone screw 102, and the bone screw head 116 is exposed. As such, the user may remove the delivery mechanism 104, and then detach the other components of the deployment system so to leave the implant 200 anchored to the facet joint via the bone screw 102. FIG. 12 shows the disclosed bone screw 102 anchoring the facet joint implant 200 to a vertebra of a facet joint.

Referring again to FIGS. 8A-8B, in operation, the implant delivery device 300 may be deployed using a guide tool 904. The guide tool 904 may include opposed prongs 922 for stabilizing the facet joint implant 200 within a facet joint, as the bone screw 102 secures the implant 200 to the vertebra. The guide tool 904 may include a shaft with a lumen 901 therein, and the implant delivery device 300 may extend through the lumen 901. The guide tool 904 is further described in detail with reference to FIGS. 13-21B.

As can be understood from FIGS. 13-21B, a distraction system 900 is configured to minimally invasively or percutaneously deliver implementations of the spinal implant 200 into a spinal facet joint space via, for example, a posterior approach. In one implementation, the system 900 includes a delivery tool 902 and a guide tool 904, both of which extend from a respective leading distal end 906, 907 to a respective trailing proximal end 908, 909. As can be understood from FIG. 9, the delivery tool 902 can be received in the lumen of the guide tool 904 to bring about the delivery of the implant 200 into the target spinal facet joint. The system 900 may further include a decorticator 936, an injector 948, a chisel 960, a place holding chisel 974, and a mallet 980.

Figure 13:
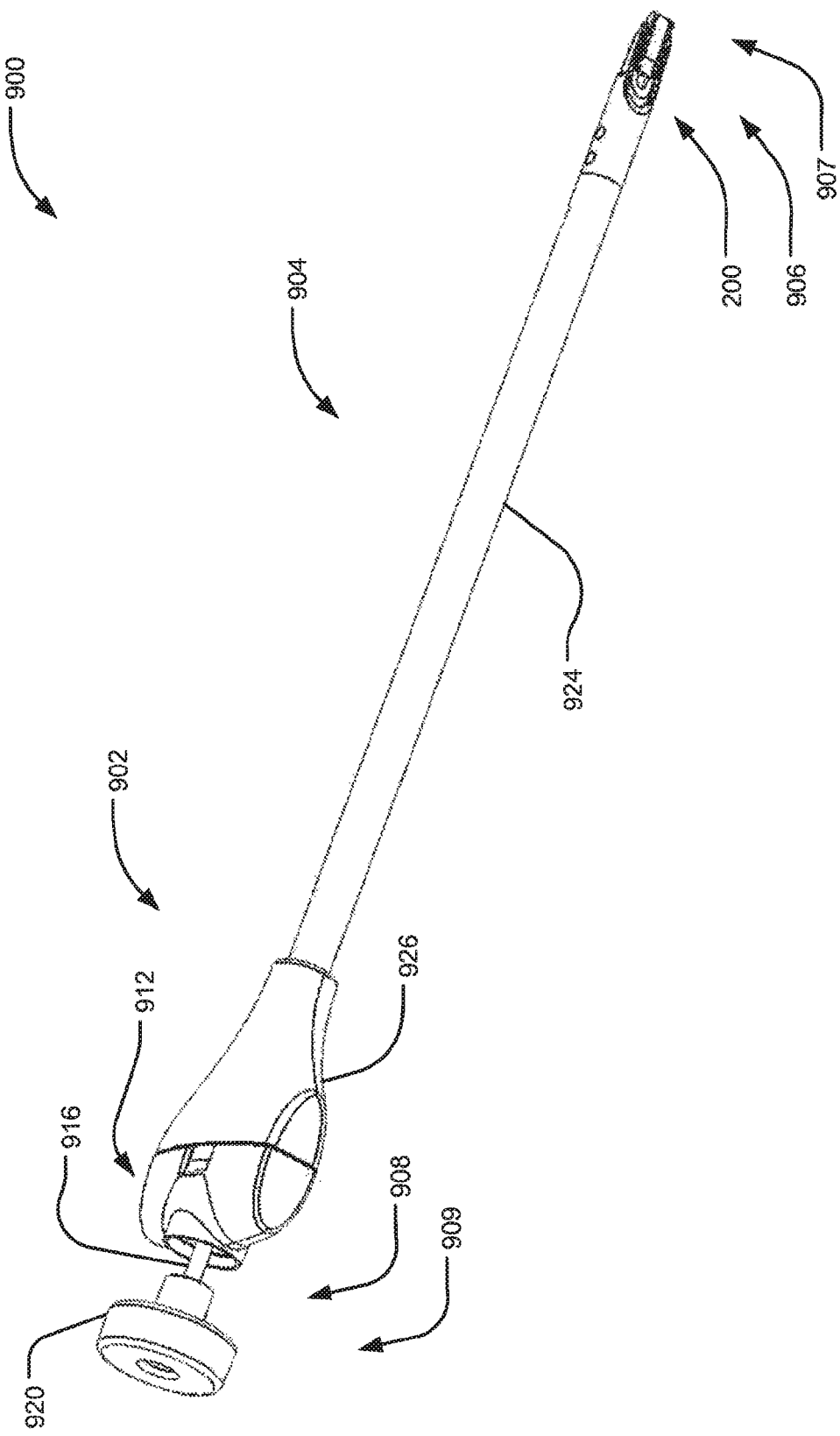
FIG. 13 is an example delivery device and guide tool configured to minimally invasively deliver a facet joint implant, according to certain embodiments.
Figure 14:
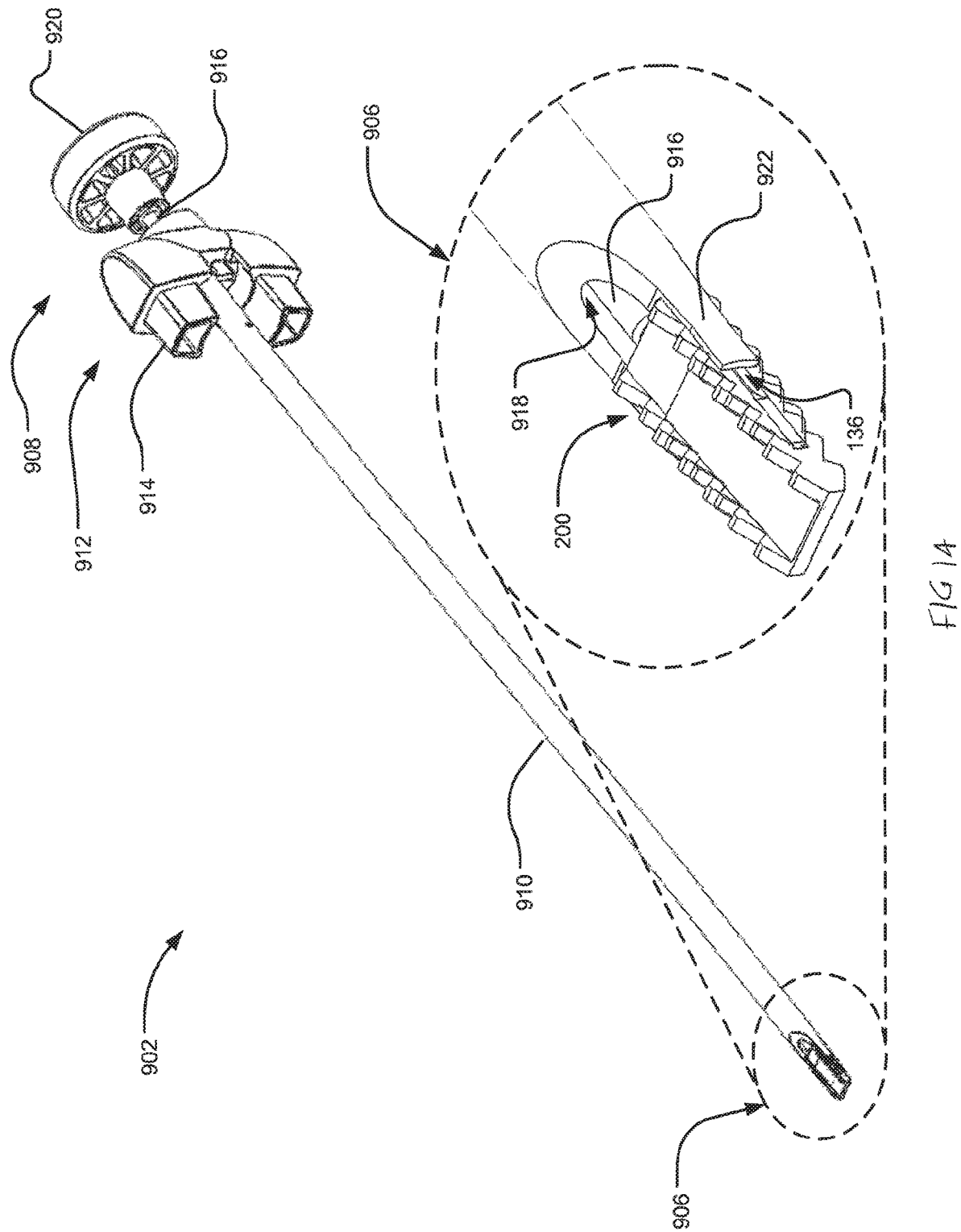
FIG. 14 is a perspective view of the delivery device of FIG. 13 and a detailed view of a distal end of the delivery device.

For a detailed description of the delivery tool 902, reference is made to FIG. 14. In one implementation, the delivery tool 902 includes a tubular body 910 with a handle arrangement 912 at the trailing proximal end 908. The handle arrangement 912 may further include one or more members 914 for engaging the guide tool 904, as can be understood from FIG. 13. In one implementation, a plunger 916 extends through a lumen 918 of the tubular body 910 and includes a handle 920 at the trailing proximal end 906. The plunger 916 may be used to distally push the implant from an interference fit engagement with the arms 922 of the delivery tool distal end 906.

In one implementation, the tubular body 910 at the leading distal end 906 includes opposed prongs 922 between which the implant, including the distal leading portion 100 and the proximal trailing anchor portion 200, may be supported. The prongs 922 include longitudinally extending ridges that are adapted to be received into and engage the respective slots 136 and 220 of the implant 200. In one implementation, the plunger 916 is spring biased to keep the plunger 916 proximally displaced in the lumen 918 of the tubular body 910, such that distal force exerted against the handle 920 causes the plunger 916 to distally displace to eject the implant from the tubular body 910 at the leading distal end 906.

Figure 15:
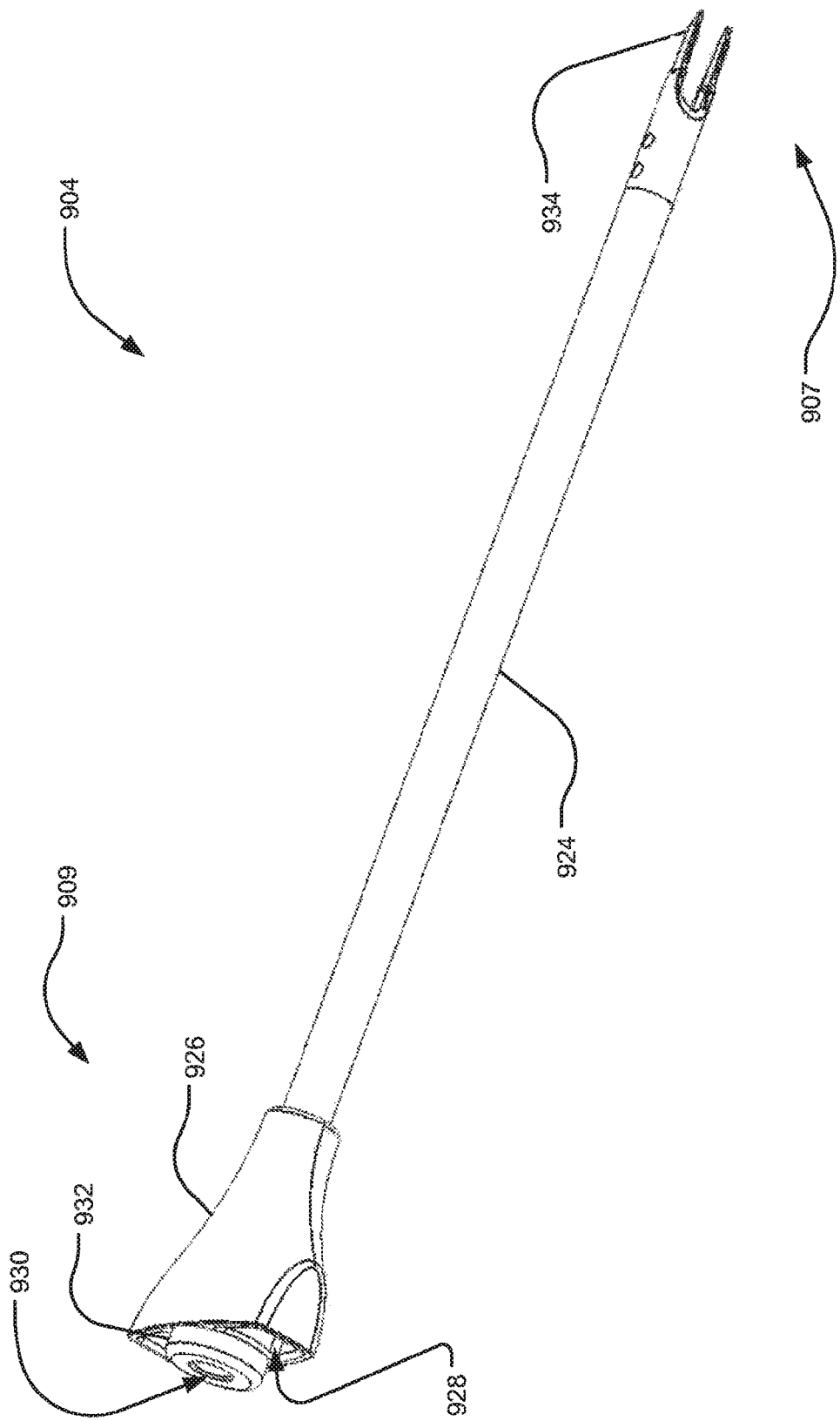
FIG. 15 is a perspective view of the guide tool of FIG. 13.

Turning to FIG. 15, a detailed description of the guide tube or tool 904 is provided. In one implementation, the guide tool 904 includes a receiving assembly 926 at a proximal end 909 and a pair of anchoring forks 934 at a distal end 907 with a generally tubular shaft 924 extending there between. The anchoring forks 934 may be textured distal parallel prongs for accessing a spinal facet joint and through which the delivery tool 902 can be routed to deliver the implant 200 in the facet joint.

The guide tool 904 can also include a malleting anvil 930 having a raised surface 932 positioned on the proximal face of the receiving assembly 926 adapted for contact with a distal end of a malleting head 966 on the chisel 960 or on the delivery tool 902. Malleting on the proximal end of the chisel 960 or the delivery tool 902 can cause longitudinal forces along the length of the respective tool piece. These longitudinal forces can be transferred, at least partially, through the contact between the malleting head and the malleting anvil 930. Accordingly, relative motion between the respective tool piece and the guide tool 904 can be prevented. As such, for example, at the distal end 907 of the guide tool 904, the relative position of the distal end 972 of the chisel 960 or the delivery tool 902 relative to the distal end 907 of the guide tool 904 can be maintained. Further, in one implementation, the receiving assembly 926 includes a receiving portion 928 for receiving and engaging the members 914 or 970 of the delivery tool 902 and the chisel 960, respectively, as can be understood from FIG. 13.

Figure 16:
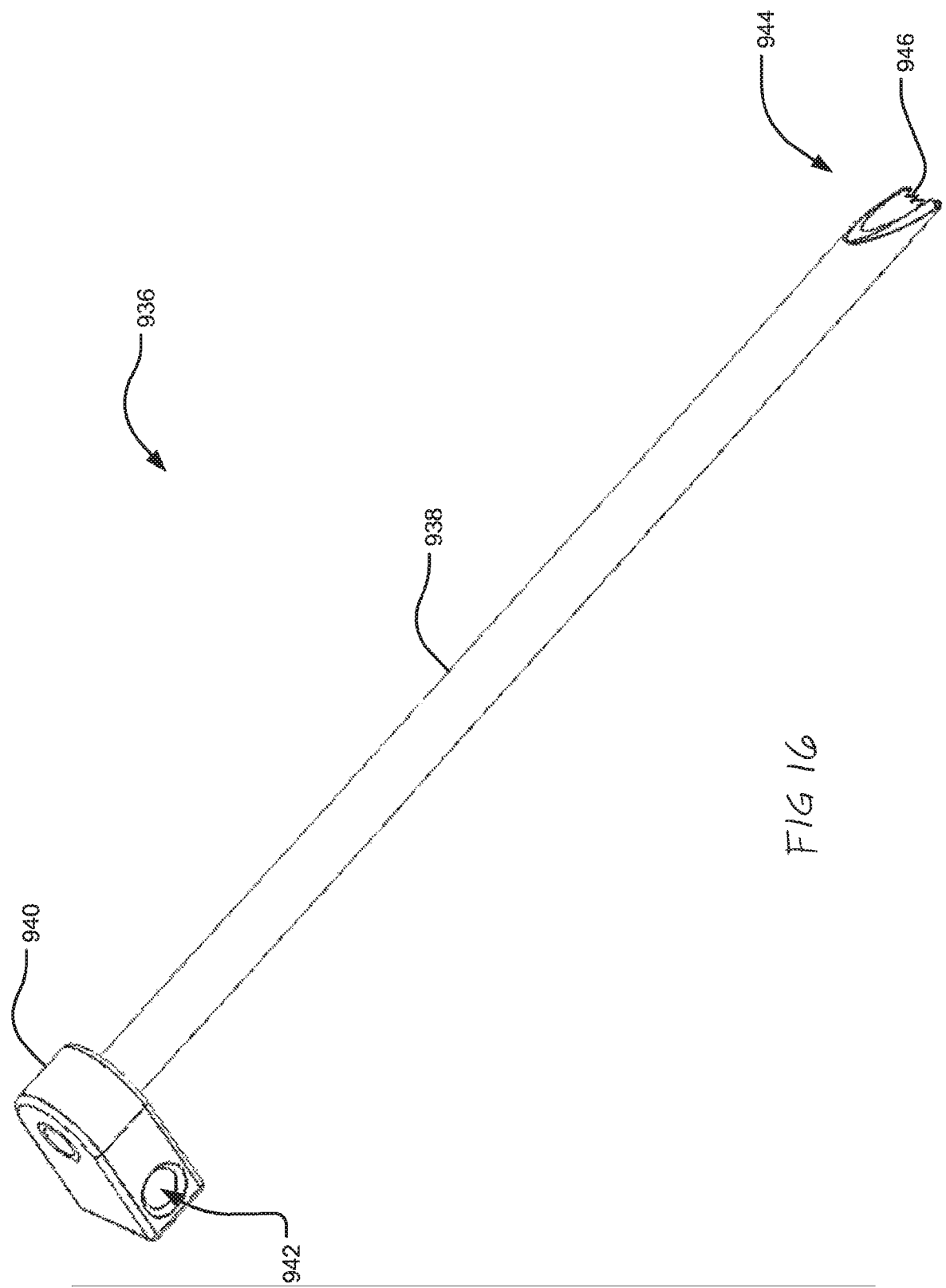
FIG. 16 is a perspective view of an example decorticator.

As can be understood from FIG. 16, in one implementation, the decorticator 936 includes a tubular shaft portion 938, an abrasive distal end 944, and a handle 940 at a proximal end. The tubular shaft 938 may have an inner radius substantially equal to an outer radius of the shaft 976 of the place holding or guide chisel 974 of FIG. 19 and may allow for sliding movement of the decorticator 936 along the length of the chisel shaft 976 and rotationally around the chisel shaft 976. In some implementations, the inner radius of the tubular shaft 938 may be slightly or substantially larger than the outer radius of the shaft 976 of the chisel 974 allowing for more freedom of movement of the decorticator 936.

The abrasive distal end 944 of the decorticator 936 may include serrated teeth 946 as shown, or may include a more flat annular surface with a gritty surface. In the implementation shown in FIG. 16, the distal end of the tubular shaft portion 938 is chamfered and the serrated teeth 946 are located on the distal-most end of the chamfered end, allowing for a more directed and controllable decorticating process. As such, the decorticator 936 shown is well suited for the intra facet process reflected by many of the implementations described herein.

Additionally, to properly place the prongs 934 of the place holding guide chisel 974 within the joint, the guide chisel 974 may be positioned substantially parallel to articular surfaces of the facet joint. As such, the place holding or guide chisel 974 may not be positioned perpendicular to the lateral masses of the facet joints and may actually be directed with a downward slope as it extends in the distal direction. Where the decorticator 936 has a non-chamfered annular end, depending on anatomy, the decorticator 936 may be able to be placed in contact with the superior lateral mass, but may be unable to reach or contact the inferior lateral mass. In the present implementation, the chamfered end of the tubular shaft portion 938 will allow the distal tip of the chamfered end to reach and decorticate the inferior lateral mass. This chamfered distal end may define an angle to the longitudinal axis. Additionally, the teeth 946 may be relatively large or they may relatively small and may extend along the full perimeter surface of the chamfered end rather being positioned solely at the tip of the chamfered end. Additionally, a beveled edge may run along the periphery of the chamfered end. That is, along the ovular shape created by the chamfered tubular shaft portion 938, the edge is beveled. As such, when the chisel 974 is inserted into the patient and/or when the decorticator 936 is advanced along the chisel 974, the beveled edge may assist in avoiding tissue snags, and the decorticator 936 may be placed in contact with the lateral mass of the facet joints in a much smoother process and may avoid damage to neighboring tissues.

The handle 940 of the decorticator 936 may include a gripping surface along its peripheral edge and may receive the tubular shaft portion 938 in a sleeve-like manner. The handle 940 may also include radially extending bores 942 adapted to receive a gripping tool to provide for better control and a higher amount of torsional leverage when decorticating the lateral masses of the facet joint or to allow for malleting in the longitudinal direction of the decorticator 936 to cause forceful decortication of the lateral mass. The decorticator 936 may then be retracted, rotated to a new radial position, advanced, and struck again for additional decortication.

Figure 17:
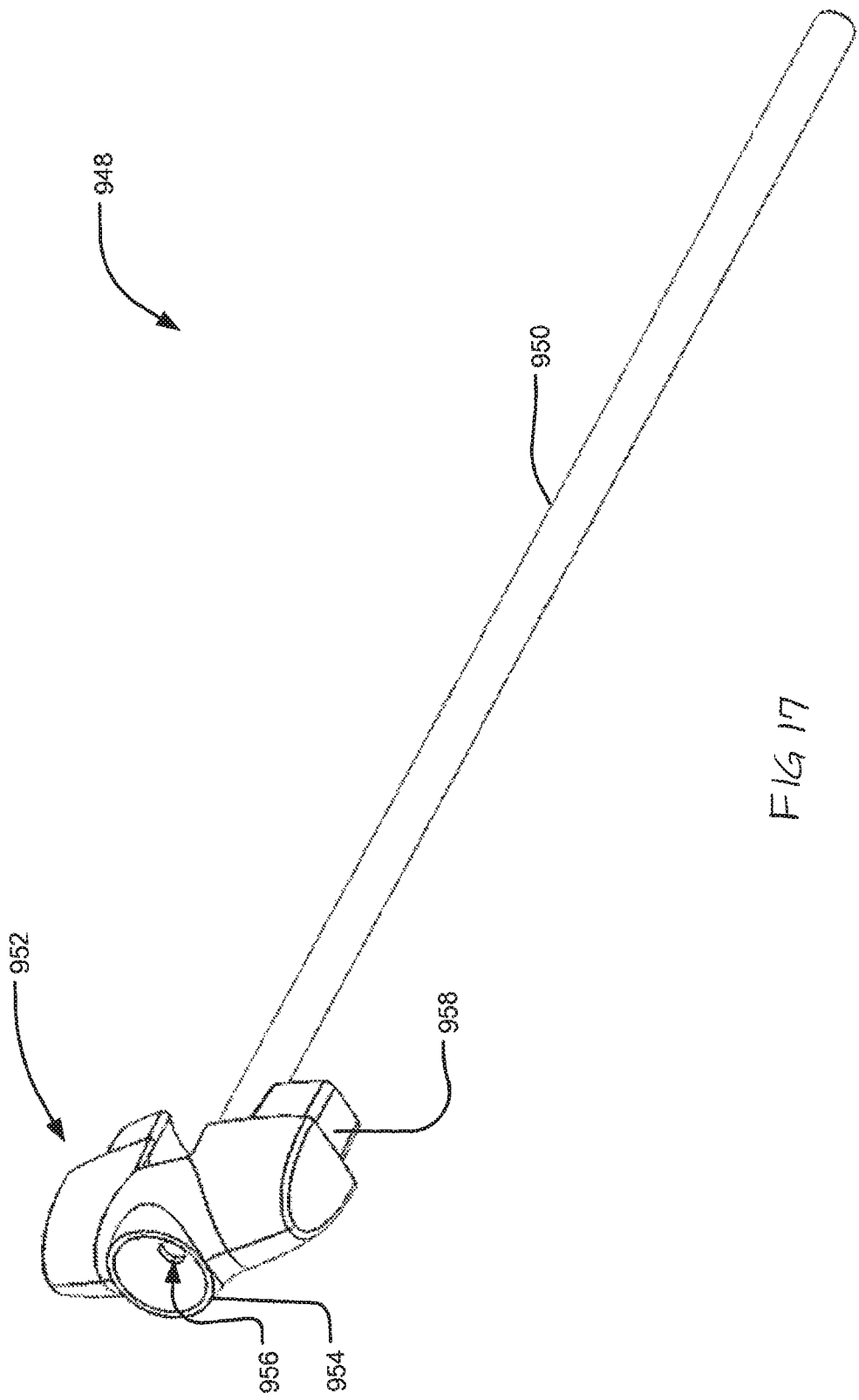
FIG. 17 is a perspective view of an example injector.

Referring to FIG. 17, in one implementation, the injector 948 includes a longitudinal delivery shaft 950 and a seating feature 952. The longitudinal delivery shaft 950 may have any cross-section shape and size adapted to fit within the guide tool 904. The longitudinal shaft 950 may have an opening 956 on its distal end 954 for directing bone paste out the distal end of the shaft 950 allowing the paste to flow into and/or over the facet joint and/or outward toward the lateral mass of a facet joint. The seating feature 952 may include a member 958 positioned around the shaft 950, which may be sized and shaped to abut the receiving portion 928 of the guide tool 904. The injector 948 may be inserted into the guide tool 904 and advanced, such that the distal end of the shaft 950 is positioned between the prongs 934.

Figure 18:
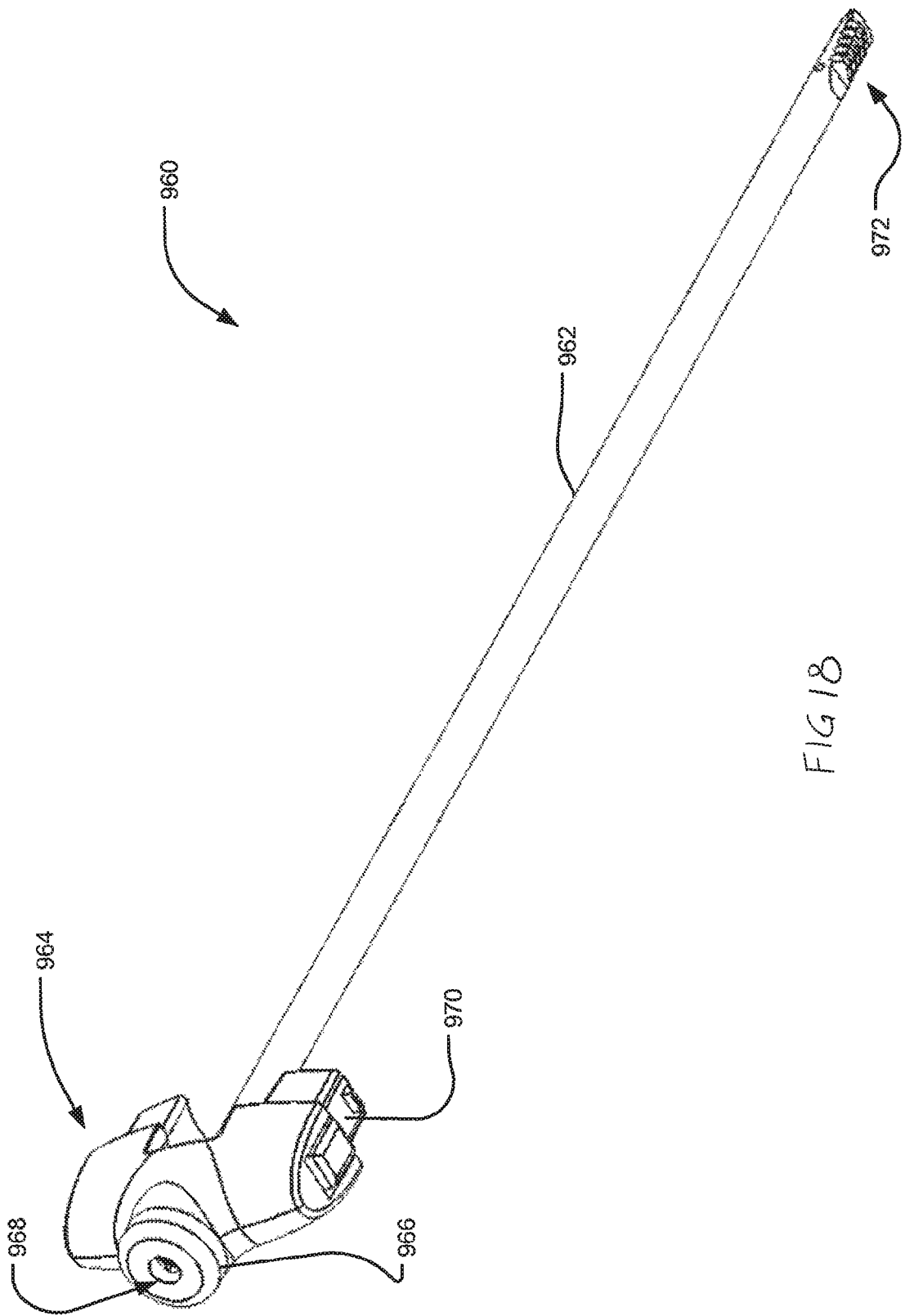
FIG. 18 is a perspective view of an example chisel.

As can be understood from FIG. 18, in one implementation, the chisel 960 includes a generally cylindrical cross-section forming a shaft 962, which may have a radius substantially equal to the inner radius of the tubular shaft portion 924 of the guide tool 904 allowing for slidable insertion of the chisel 960 within the guide tool 904. Alternatively, the radius of the shaft 963 may be smaller than the inner radius of the tubular shaft 924 providing for more play and adjustability of the chisel 960 and the guide tool 904 relative to one another. The chisel 960 may include a single or doubly chamfered tip 972 at a distal end or may have a coped distal end or a combination of coping and chamfering. The tip 972 may include a roughened surface on one or more sides to aid in anchoring or docking the chisel in the facet joint. Additionally, this roughened surface may allow for roughening or decorticating the inner surfaces of the facet joint. The tip 972 may have a length adapted to extend substantially across the facet joint.

The chisel 960 may further include a handle assembly 964 that may include a member 970 positioned around the shaft 962, which may be sized and shaped to abut the receiving portion 928 of the guide tool 904. The chisel 1008 may also include a longitudinally extending lumen 968 and a malleting head 966.

Figure 19:
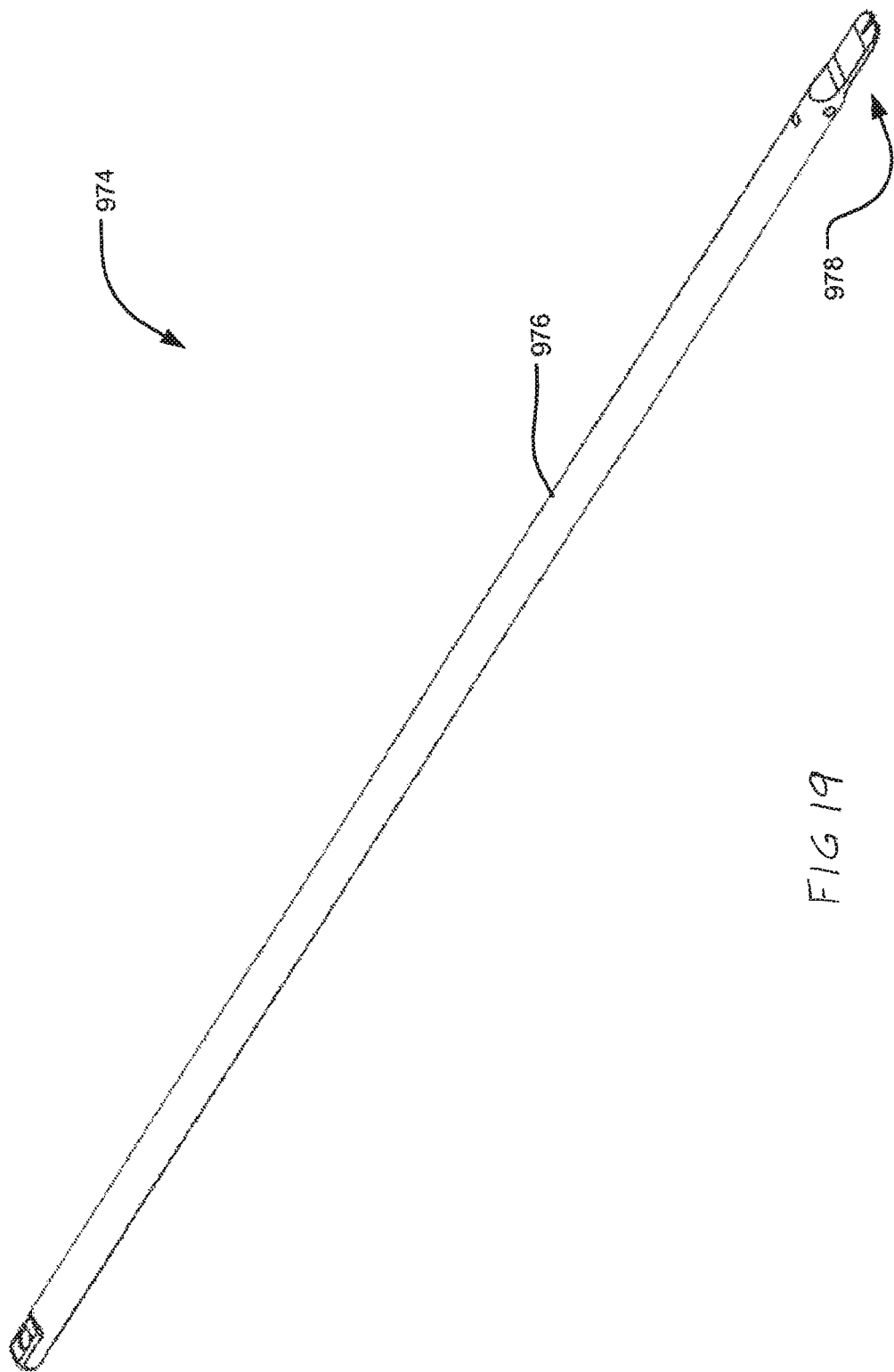
FIG. 19 is an example place holding chisel.

Turning to FIG. 19, in one implementation, the placing holding or guide chisel 974 includes a shaft 976 and a distal tip 978, which may include a tip the same or similar to the chisel 960. For example, the chisel 974 can include a coped and/or chamfered tip. Additionally, the chisel 974 can include ridges. Additionally, the chisel 974 can include a radiopaque portion on the shaft 976 adapted to allow recognition of the location of the chisel 974 while avoiding occlusion of the lateral view. The radiopaque portion can include a straight, round, square, or other shaped piece of material positioned near the distal end of the chisel 974 for locating the distal end. As also shown, the proximal end of the chisel 974 can include a hole extending transversely therethrough. The hole can adapted to receive a transverse rod or shaft extending into the hole and/or through the hole. The rod or shaft and the chisel 974 can form a T-grip or L-shaped grip for use in pulling on the chisel 974 for removal.

In one implementation, the place holding chisel 974 can be used as a place holder without occluding the lateral view of a chisel and delivery tool positioned in a contralateral facet joint. That is, upon placement of the chisel 960 and the guide tool 904 in a first facet joint, the chisel 960 may be removed and replaced with the place holding chisel 974 where the prongs 934 of the guide tool 904 maintain the position of the system 900. The guide tool 904 may also be removed and reassembled with the chisel 960 once the place holding chisel 974 is properly positioned. The guide tool 904 and chisel 960 may then be inserted into the contralateral facet joint or second joint. By replacing the chisel 960 in the first joint with the place holding chisel 974, the location of the chisel 960 and guide tool 904 in the second joint may be more readily ascertainable using lateral fluoroscopy. That is, if a radiopaque chisel or delivery device was left in place in the first joint, the fluoroscopic view of the contralateral facet joint would be relatively occluded. Upon placing the guide tool 904 properly in the second facet joint, the procedure above may continue. Upon completing treatment of the second facet joint, the guide tool 904 may be sleeved over the place holding chisel 974 still positioned in and holding the place in the first facet joint and the first facet joint may then be treated with the above procedure. It is noted that initial placement of the guide tool 904 can be conducted with the place holding chisel 974 rather than the chisel 960 to avoid having to replace the chisel 960.

Figure 20:
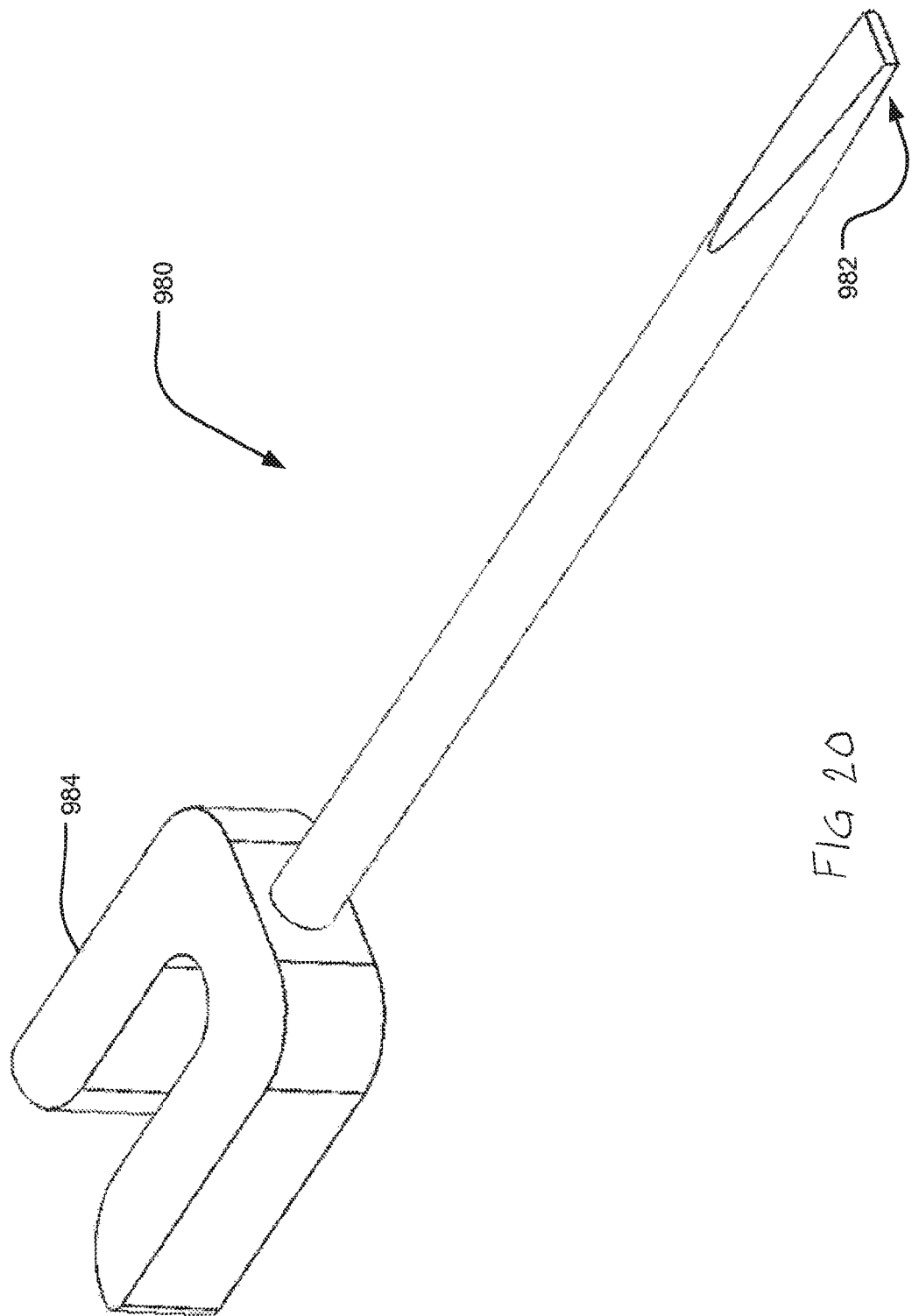
FIG. 20 is a perspective view of an example malleting tool.

Referring to FIG. 20, in one implementation, the malleting tool 980 can include a longitudinally shaped shaft with a U-shaped decorticator interface 984 at one end and a chamfered tip 982 at the other end. The decorticator interface 984 can be adapted for positioning around the guide tool 904 in a position just proximal to a malleting element of the decorticator 936. The u-shape of the decorticator interface 984 may allow the malleting tool 980 to be placed in position from the side of the guide tool 904 and selectively used as required to forcibly advance the decorticator 936.

The chamfered end of the tool 982 can be held in position while the user mallets near the decorticator interface end causing the interface 984 to contact the malleting element on the decorticator 936. The decorticator 936 may then be retracted, rotated to a new radial position, advanced, and struck again for additional decortication. The malleting tool 980 may rotate with the decorticator 936 or it may remain in a position convenient for malleting. In addition to malleting, the malleting tool 980 can be used to assist in separating several tools. That is, in some cases, the handles of a given tool piece can be difficult to separate from receiving portion. The chamfered tip 982 can be used to wedge between a given handle and the receiving portion to assist in separating the devices.

Other implementations of a distraction system 900 can be configured with alternative retaining and deployment (release or eject) methods, such as screw drives, latches, snaps, cams, adhesives, magnets, or the like.

The delivery system components depicted in FIGS. 13-20 can be used to minimally invasively implant an implant 200 in a spinal facet joint that is the target of treatment. For example, in one embodiment, a percutaneous or minimally invasive incision is made in the posterior region of the neck to lead to the target facet joint. The access chisel 974 depicted in FIG. 19 is routed through incision under fluoroscopic guidance until the tapered distal tip 978 resides in the target facet joint and the chisel shaft 976 extends out of the patient via the incision. With the access chisel 974 so positioned, the outer decorticator 936 of FIG. 16 can be grasped and distally routed over the access chisel 974 such that the chisel shaft 976 is received in the lumen that extends longitudinally through the outer decorticator 936. With the distal decorticating end 946 of the outer decorticator 936 abutting against one or more lateral masses adjacent the target facet joint, the outer decorticator 936 can be rotated about the chisel shaft 976 to decorticate the bone surfaces of the lateral masses adjacent the target facet joint. Once decortication of the lateral masses has been sufficiently achieved, the decorticator 936 can be removed from about the chisel shaft 976 and from the patient.

With the place holding or access chisel 974 so positioned, the guide tool 904 of FIG. 15 is grasped and distally routed over the chisel 974 such that the chisel shaft 976 is received in the guide tool lumen that extends longitudinally through the guide tool shaft 924. The tapered forked distal end 907 of the guide tool 904 is distally advanced through the incision and along the chisel shaft 976 until the tapered forks 934 of the guide tool 904 are positioned inside the target facet joint, the chisel tapered distal tip 978 being located between the pair of forks 934 of the guide tool distal end 907, the guide tool shaft 924 extending out of the patient via the incision.

With the guide tool 904 so positioned, the place holding or access chisel 974 can be withdrawn out of the guide tool lumen and out of the patient, leaving the guide tool tapered forked distal end 907 residing in the target facet joint and the guide tool shaft extending out of the patient. The decorticating chisel 960 of FIG. 18 can then be distally routed through the lumen of the guide tool 904 to place the tapered decorticating distal end 972 of the chisel 960 between the guide tool forks 934 located in the target facet joint space. The decorticating chisel 960 can then be displaced distal-proximal to cause the tapered decorticating distal end 972 of the chisel 960 to remove the cartilage of the target facet joint space located between the guide tool forks 934 and further decorticate any associated bone surfaces of the target facet joint space. Once the target facet joint space surfaces have been prepped with the decorticating chisel 960, the chisel 960 can be removed from the lumen of the guide tool 904 and the patient.

The implant 200 is coupled to, and supported off of, the distal end 906 of the implant delivery tool 902 of FIG. 14. As discussed above, the coupling of the implant delivery tool distal end 906 with the implant 200 may be achieved via interference fit engagement. With the implant supported off of the distal end 906 of the implant delivery tool 902 in a manner similar to that depicted in FIG. 14, the implant 200, and the delivery tool shaft 910 on which the implant 200 is supported, are distally routed through the lumen of the guide tool 904 until the implant 200 and the delivery tool distal end 906 are located in the target facet joint space between the pair of forks 934 of the guide tool distal end 907, the delivery tool 902, the guide tool 904 and the implant 200 being coupled together as depicted in FIG. 13. With the implant 200 so positioned in the target spinal facet joint space, the plunger 916 may be used to deposit the implant 200 into the target spinal facet joint space by plunging the implant 200 from the delivery tool distal end 906 via corresponding manipulation of the plunger 916 via its handle 920. Once the implant 200 is decoupled from the delivery tool 902 and deposited into the facet joint space, the delivery tool 902 can be withdrawn from the guide tool 904, which is left in place with its forked distal end 907 occupying the facet joint space and the implant 200 being located between the forks 934 of the guide tool 904.

Figure 21A:
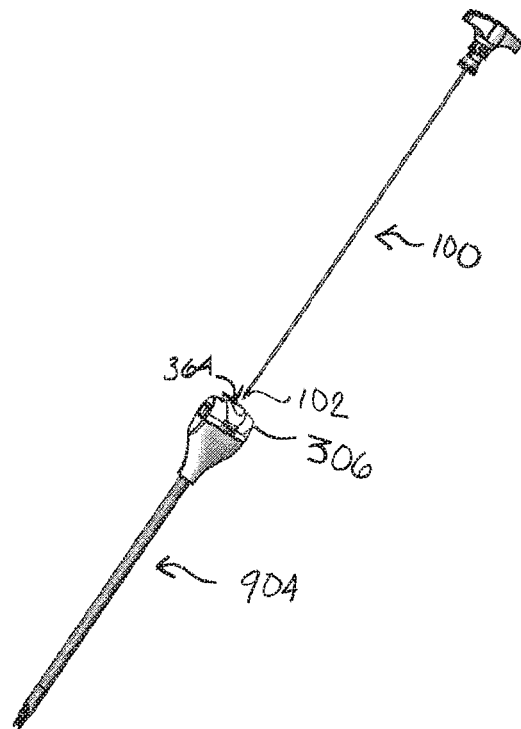
FIGS. 21A-21B are perspective views of the implant delivery device of FIGS. 7A-7B, assembled within the guide tool of FIG. 13, and the bone screw device of FIG. 1, according to certain embodiments.
Figure 21B:
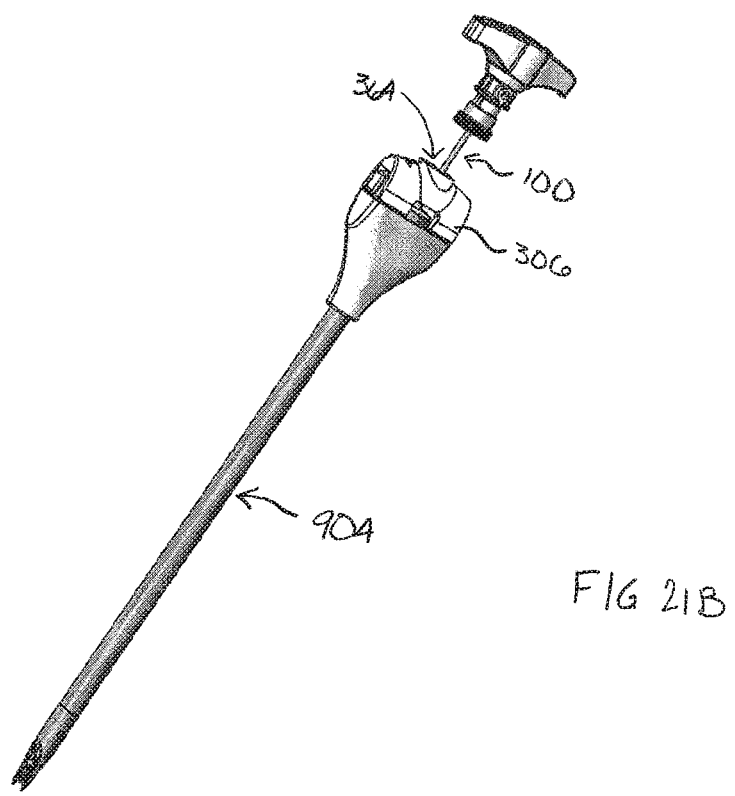

Now turning to FIGS. 21A-21B, when the delivery tool 902 is withdrawn from the guide tool 904, and the implant 200 is located between the forks of the guide tool 904, a user may insert the implant delivery device 300 through the lumen of the guide tool 904 to deliver the bone screw 102 and thus anchor the implant 200 to the vertebra. For example, a user may insert the implant delivery device 300 through the lumen of the guide tool 904 such that the distal end of the inner guide tube 350 is proximate the facet implant 200. The user may insert the bone screw device 100 through a proximal end 364 of the inner guide tube 350 and advance the bone screw device 100 through the proximal portion 352 of the inner guide tube 350 along a first trajectory. The user may continue to advance the bone screw device 100 through the inner guide tube 352, and the bend 356 within the guide tube may cause the flexible region 126 of the delivery mechanism 104 to flex. Thus, the bone screw 102 may exit the distal end 358 of the inner guide tube 350 along a second trajectory so that the bone screw 102 is directed to the inlet 210 of the implant screw cavity 220. When the bone screw 102 is within the screw cavity 220, the user may rotate the bone screw device 100 to cause the bone screw 102 to advance through implant 200 and into the vertebra. The bone screw 102 may advance through the implant 200 and into the vertebra along a third trajectory. As the user further screws the screw 102 into the implant 200 and vertebra, the flexible region 126 further flexes and a load is concentrated at the breakable junction 122. When the user screws the bone screw 102 a sufficient amount to anchor the implant 200 to the vertebra, the breakable junction 122 may experience a predetermined load to cause the bone screw 102 to detach from the delivery mechanism 104. The process can then be repeated for another facet joint if needed.

For a further discussion regarding delivery systems and methodology, see U.S. patent application Ser. No. 12/653, 283, which was filed on Dec. 10, 2009, and which is entitled "Verbal Joint Implants and Delivery Tools." The full disclosure of application Ser. No. 12/653,283 is hereby incorporated by reference.

Although this disclosure has focused on the description of certain embodiments and examples, the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method for implanting a bone screw in a vertebra, the method comprising:
    delivering the bone screw and a bone screw delivery mechanism near the vertebra, wherein a first end of the bone screw is attached to a second end of the bone screw delivery mechanism at a breakable junction;
    advancing the bone screw and the bone screw delivery mechanism to contact the vertebra, wherein the bone screw is advanced at a first angle relative to a longitudinal axis extending through a facet joint implant located in a facet joint formed by the vertebra and an adjacent vertebra;
    rotating the bone screw delivery mechanism to cause the bone screw to screw into the vertebra;
    detaching the bone screw delivery mechanism from the bone screw by breaking at the breakable junction;
    delivering a second bone screw and a second bone screw delivery mechanism near the adjacent vertebra, wherein an end of the second bone screw is attached to an end of the second bone screw delivery mechanism at a breakable junction;
    advancing the second bone screw and bone screw delivery mechanism to contact the adjacent vertebra, wherein the second bone screw is advanced at a second angle relative to a longitudinal axis extending through the facet joint implant located in the facet joint formed by the vertebra and the adjacent vertebra;
    rotating the second bone screw delivery mechanism to cause the second bone screw to screw into the adjacent vertebra; and
    detaching the second bone screw delivery mechanism from the second bone screw by breaking at the breakable junction.

2. The method of claim 1, wherein breaking at the breakable junction comprises breaking the bone screw delivery mechanism off of the bone screw by screwing the bone screw into the vertebra until a break in the junction occurs.

3. The method of claim 1, wherein breaking at the breakable junction comprises breaking the bone screw delivery mechanism off of the bone screw by applying force to the bone screw delivery mechanism until a break in the junction occurs.

4. The method of claim 1, wherein the bone screw and the bone screw delivery mechanism comprise a one-piece device with the breakable junction between the bone screw and the bone screw delivery mechanism.

5. The method of claim 1, further comprising advancing the bone screw through an opening in a facet joint implant located in a facet joint formed by the vertebra and an adjacent vertebra.

6. The method of claim 5, wherein the facet joint implant is formed by bone or bone substitute material.

7. The method of claim 1, wherein the first angle is different from the second angle.

8. A method for implanting a bone screw through a facet joint implant to attach to a vertebra, the method comprising:
  inserting a bone screw device near the vertebra, the bone screw device having an elongate shaft portion and a bone screw portion, wherein the elongate shaft portion and the bone screw portion comprise a one-piece device with a breakable junction between them;
  advancing the bone screw device through an opening in the facet joint implant at an angle relative to a longitudinal axis extending through the facet joint implant;
  rotating the bone screw device to cause the bone screw portion to screw into the vertebra to secure the facet joint implant to the vertebra;
  breaking the elongate shaft portion of the bone screw device off of the bone screw portion at the breakable junction located between the two portions,
  inserting a second bone screw device near a second vertebra, the second bone screw device having an elongate shaft portion and a bone screw portion, wherein the elongate shaft portion and the bone screw portion comprise a one-piece device with a breakable junction between them;
  advancing the second bone screw device through an opening in the facet joint implant at a second angle relative to a longitudinal axis extending through the facet joint implant;
  rotating the second bone screw device to cause the bone screw portion to screw into the vertebra to secure the facet joint implant to the second vertebra; and
  breaking the elongate shaft portion of the second bone screw device off of the bone screw portion at the breakable junction located between the two portions.

9. The method of claim 8, wherein breaking the elongate shaft portion off of the bone screw portion comprises screwing the bone screw portion into the vertebra until a break in the breakable junction occurs.

10. The method of claim 8, wherein breaking the elongate shaft portion off of the bone screw portion comprises applying force to the elongate shaft portion until a break in the breakable junction occurs.

11. A method for implanting a bone screw in a vertebra at or immediately adjacent a facet joint implant positioned in a spinal joint formed by the vertebra and an adjacent vertebra, the method comprising:
  inserting a bone screw delivery mechanism near the spinal joint, wherein a first end of the bone screw is coupled to a second end of a bone screw delivery mechanism at a breakable junction;
  advancing the bone screw delivery mechanism at an angle relative to a longitudinal axis extending through the facet joint implant to cause the bone screw to engage the vertebra to help secure the spinal joint implant within the spinal joint; and
  separating the bone screw delivery mechanism from the bone screw by breaking at the breakable junction,
  inserting a second bone screw delivery mechanism near the spinal joint, wherein an end of a second bone screw is coupled to an end of the second bone screw delivery mechanism at a breakable junction;
  advancing the second bone screw delivery mechanism at a second angle relative to a longitudinal axis extending through the facet joint implant to cause the second bone screw to engage the vertebra or the adjacent vertebra to help secure the facet joint implant within the spinal joint; and
  separating the second bone screw delivery mechanism from the second bone screw by breaking at the breakable junction.

12. The method of claim 11, wherein advancing the bone screw delivery mechanism comprises advancing at least the bone screw through an opening in the facet joint implant to screw into the vertebra.

13. The method of claim 11, wherein the spinal joint comprises a facet joint.

14. The method of claim 11, wherein advancing the bone screw delivery mechanism comprises advancing at least the bone screw through an opening in the facet joint implant and rotating the bone screw to screw into the vertebra.

* * * * *